United States Patent
Augustine

(10) Patent No.: US 7,871,428 B2
(45) Date of Patent: *Jan. 18, 2011

(54) SURGICAL BARRIER DEVICE INCORPORATING AN INFLATABLE THERMAL BLANKET WITH AN ATTACHED SURGICAL DRAPE

(75) Inventor: Scott Douglas Augustine, Bloomington, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 1096 days.

This patent is subject to a terminal disclaimer.

(21) Appl. No.: 11/511,918

(22) Filed: Aug. 28, 2006

(65) Prior Publication Data
US 2006/0293735 A1    Dec. 28, 2006

Related U.S. Application Data

(60) Division of application No. 09/771,791, filed on Jan. 29, 2001, now Pat. No. 7,108,713, which is a continuation of application No. 09/286,714, filed on Apr. 5, 1999, now Pat. No. 6,203,567, which is a continuation of application No. 08/867,092, filed on Jun. 2, 1997, now Pat. No. 5,941,907.

(51) Int. Cl.
*A61F 7/00* (2006.01)
(52) U.S. Cl. .................. 607/107; 607/96; 607/104
(58) Field of Classification Search .............. 607/104, 607/105, 107
See application file for complete search history.

(56) References Cited

U.S. PATENT DOCUMENTS

| | | | |
|---|---|---|---|
| 222,690 A | 12/1879 | Goldschmidt | |
| 1,399,095 A | 12/1921 | Webb | |
| 1,777,982 A | 10/1930 | Popp | |
| 2,093,834 A | 9/1937 | Gaugler | |
| 2,110,022 A | 3/1938 | Kliesrath | |
| 2,122,964 A | 7/1938 | Sweetland | 34/28 |
| 2,512,559 A | 6/1950 | Williams | 5/347 |
| 2,601,189 A | 6/1952 | Wales | 4/160 |
| 2,706,988 A | 4/1955 | Weber | 128/102 |

(Continued)

FOREIGN PATENT DOCUMENTS

EP        0 113 420 A1     11/1983

(Continued)

OTHER PUBLICATIONS

Ninth New Collegiate Dictionary, definition of "laminate", p. 645.

(Continued)

*Primary Examiner*—Roy D Gibson
(74) *Attorney, Agent, or Firm*—Terrance A. Meador; INCAPLAW

(57) ABSTRACT

A surgical barrier device includes an inflatable thermal blanket with an attached surgical drape. The inflatable thermal blanket is inflatable through an inlet by a thermally-controlled inflating medium. An aperture array on the undersurface of the inflatable thermal blanket exhausts the thermally controlled inflating medium from the inflatable thermal blanket. The surgical drape extends from the inflatable thermal blanket and is sized to substantially cover the entirety of the patient's body. Where patient access is required, that drape has an opening to provide access to a surgical site.

17 Claims, 11 Drawing Sheets

U.S. PATENT DOCUMENTS

| | | | |
|---|---|---|---|
| 3,243,827 A | 4/1966 | Kintner | 5/334 |
| 3,418,726 A | 12/1968 | Sparks | 34/99 |
| 3,610,251 A | 10/1971 | Sanderson | 128/379 |
| 3,610,323 A | 10/1971 | Troyer | 165/46 |
| 3,691,646 A | 9/1972 | Ruffolo | 34/90 |
| 3,714,947 A | 2/1973 | Hardy | 128/400 |
| 3,750,664 A | 8/1973 | Collins | 128/132 D |
| 3,757,366 A | 9/1973 | Sacher | 5/347 |
| 4,572,188 A | 2/1986 | Augustine et al. | 128/380 |
| 4,660,388 A | 4/1987 | Greene, Jr. | 62/261 |
| 4,777,802 A | 10/1988 | Feher | 62/3 |
| 4,807,644 A | 2/1989 | Sandhaus | 128/849 |
| 4,867,230 A | 9/1989 | Voss | 165/46 |
| 5,125,238 A | 6/1992 | Ragan et al. | 62/259.3 |
| 5,184,612 A | 2/1993 | Augustine | 128/400 |
| 5,300,100 A | 4/1994 | Hickle et al. | 607/107 |
| 5,300,101 A | 4/1994 | Augustine et al. | 607/107 |
| 5,300,102 A | 4/1994 | Augustine et al. | 607/107 |
| 5,304,213 A | 4/1994 | Berke et al. | 607/104 |
| 5,324,320 A | 6/1994 | Augustine et al. | 607/107 |
| 5,336,250 A | 8/1994 | Augustine | 607/107 |
| 5,343,579 A | 9/1994 | Dickerhoff et al. | 5/421 |
| 5,350,417 A | 9/1994 | Augustine | 607/104 |
| 5,360,439 A | 11/1994 | Dickerhoff et al. | 607/104 |
| 5,405,370 A | 4/1995 | Irani | 607/104 |
| 5,405,371 A | 4/1995 | Augustine et al. | 607/107 |
| 5,443,488 A | 8/1995 | Namenye et al. | 607/104 |
| 5,514,169 A | 5/1996 | Dickerhoff et al. | 607/107 |
| 5,545,194 A | 8/1996 | Augustine | 607/104 |
| 5,620,482 A | 4/1997 | Augustine et al. | 607/107 |
| 5,785,716 A | 7/1998 | Bayron et al. | 607/108 |
| 5,800,483 A | 9/1998 | Vought | 607/104 |
| 5,941,907 A | 8/1999 | Augustine | 607/104 |
| 5,989,285 A * | 11/1999 | DeVilbiss et al. | 607/107 |
| 6,203,567 B1 | 3/2001 | Augustine | 607/104 |
| 7,108,713 B1 | 9/2006 | Augustine | 607/107 |

FOREIGN PATENT DOCUMENTS

| | | |
|---|---|---|
| EP | 0 311 336 B1 | 10/1988 |
| EP | 0986353 B1 | 8/2001 |
| GB | 716746 | 10/1954 |
| GB | 1 334 935 | 10/1973 |
| GB | 1 461 383 | 1/1977 |
| GB | 1 532 219 | 11/1978 |
| GB | 1 566 207 | 4/1980 |
| WO | 85/03216 A1 | 8/1985 |
| WO | 98/55058 A1 | 12/1998 |

OTHER PUBLICATIONS

Webster's Third New International Dictionary, definition of "bond", p. 250.
McGraw-Hill Encyclopedia of Science & Technology, entry for "bonding", p. 713.
International Search Report in PCT/US98/01218, mailed Apr. 29, 1998.
First Written Opinion in PCT/US98/01218, mailed Feb. 24, 1999.
Applicant's Response to the first Written Opinion in PCT/US98/01218, mailed May 20, 1999.
Second Written Opinion in PCT/US98/01218, mailed Jul. 27, 1999.
Applicant's Response to the second Written Opinion in PCT/US98/01218, mailed Aug. 26, 1999.
International Preliminary Examination report in PCT/US98/01218, mailed Sep. 8, 1999.

* cited by examiner

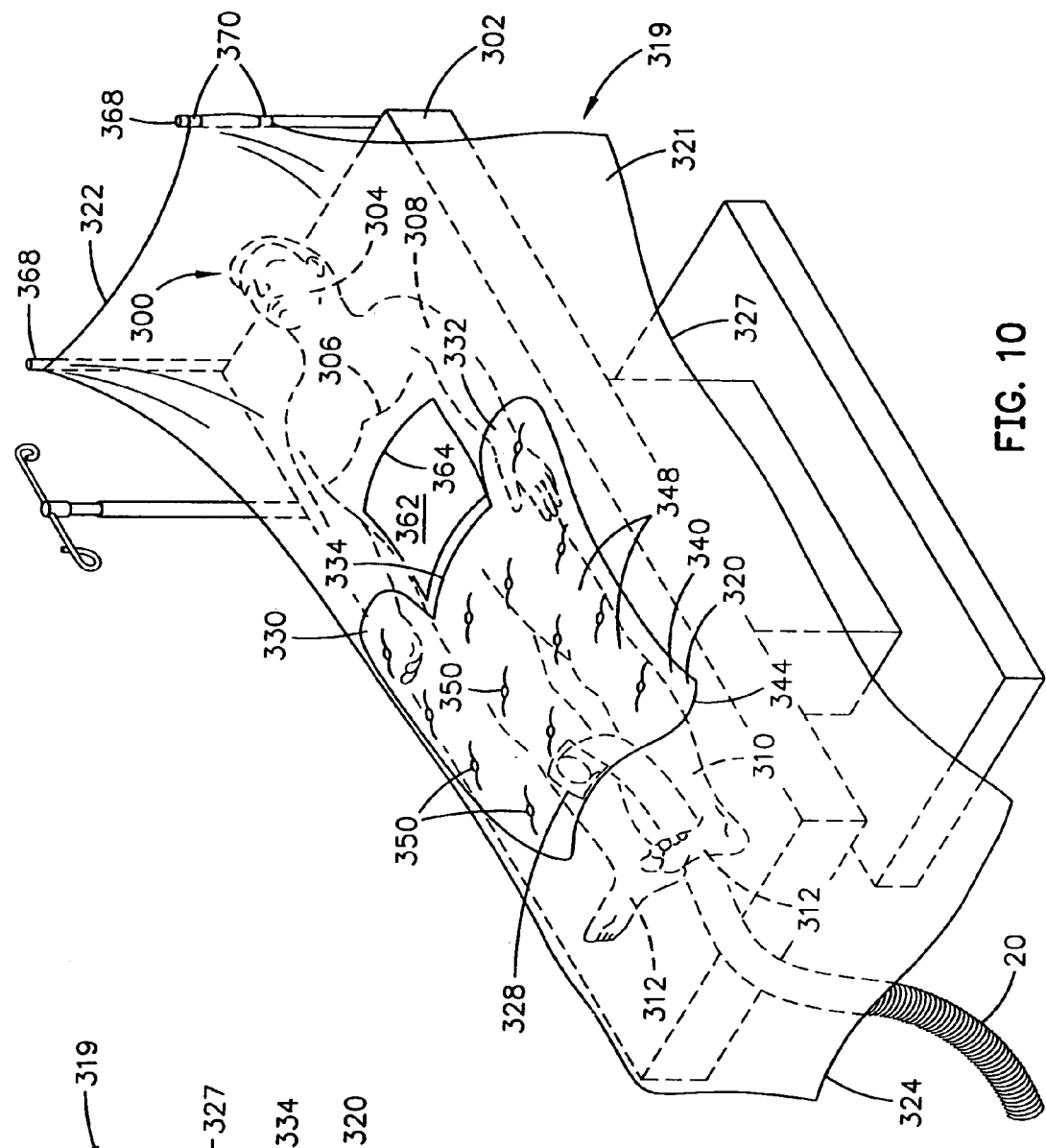
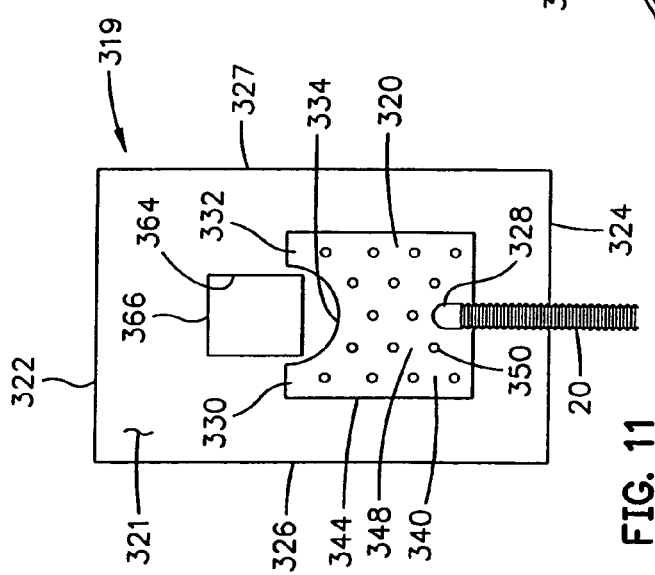
FIG. 10
FIG. 11

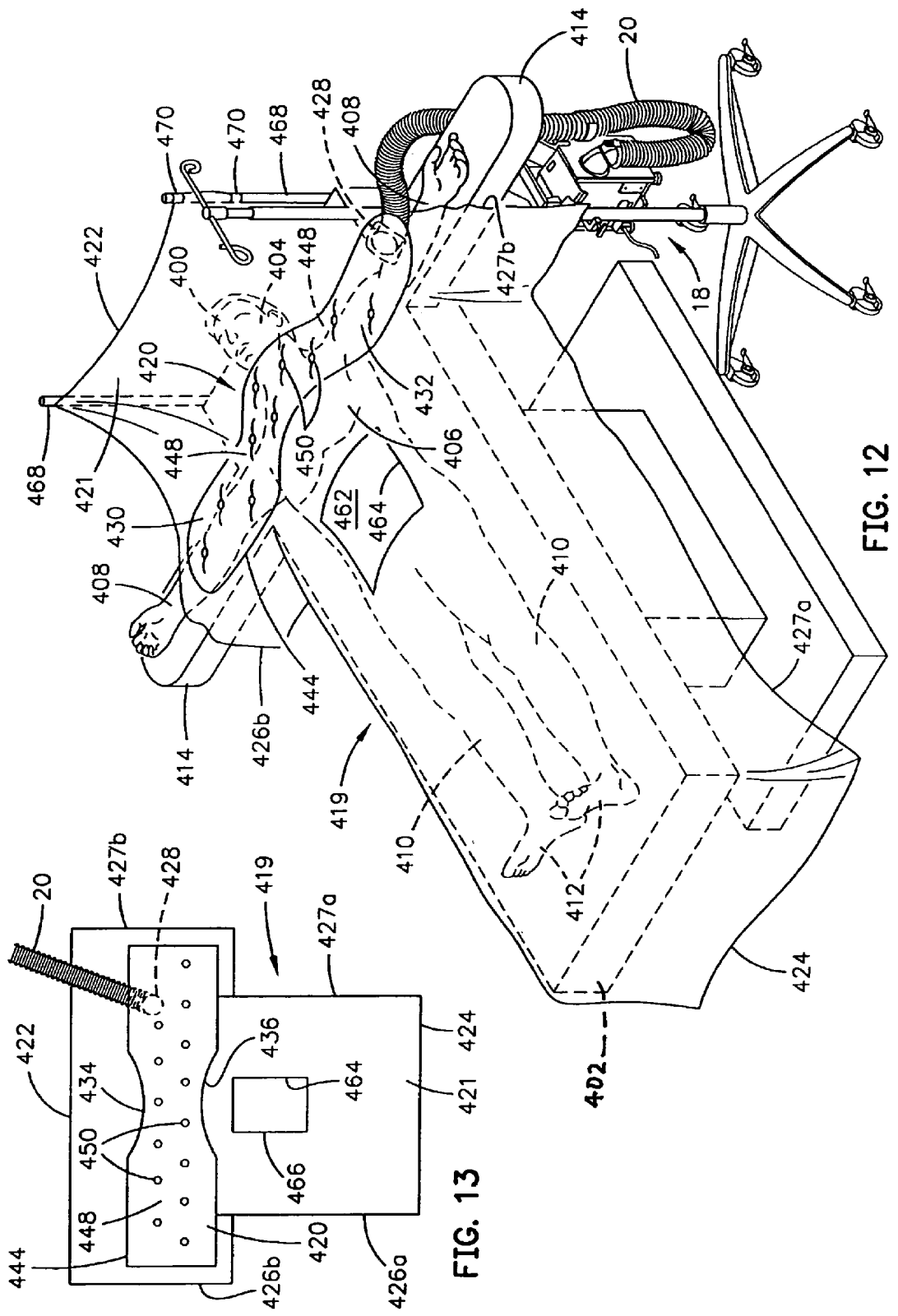

SURGICAL BARRIER DEVICE INCORPORATING AN INFLATABLE THERMAL BLANKET WITH AN ATTACHED SURGICAL DRAPE

RELATED APPLICATIONS

This is a division of U.S. patent application Ser. No. 09/771,791, filed Jan. 29, 2001, which is a continuation of U.S. patent application Ser. No. 09/286,714, filed Apr. 5, 1999, now U.S. Pat. No. 6,203,567, which is a continuation of Ser. No. 08/867,092, filed Jun. 2, 1997, now U.S. Pat. No. 5,941,907.

BACKGROUND OF THE INVENTION

1. Field of the Invention

This invention relates generally to medical devices used during surgery, including inflatable thermal blankets and surgical drapes. More particularly, the invention pertains to a surgical barrier device that incorporates an inflatable thermal blanket to control patient body temperature during a medical procedure such as surgery, and a surgical drape that provides a barrier between a surgical field and one or more other fields during surgery, while providing access to the surgical field.

2. Description of the Related Art

The inflatable thermal blanket prior art is well described in prior U.S. Pat. No. 4,572,188 entitled "AIRFLOW COVER FOR CONTROLLING BODY TEMPERATURE," and prior U.S. Pat. No. 5,620,482 entitled "INFLATABLE THERMAL BLANKET WITH A FOOT DRAPE". In these prior patents, an inflatable thermal blanket is placed over a patient and inflated by a thermally controlled inflating medium, such as warmed air. The pressure of the inflating medium causes the blanket to expel the warmed air through holes in the underside of the blanket, thereby creating an ambient environment about the patient, the thermal characteristics of which are determined by the temperature of the inflating medium. The holes open through a blanket base sheet into the interior of the blanket. Such an inflatable thermal blanket is intended, among other things, for the treatment or prevention of hypothermia, as might occur intraoperatively, or postoperatively.

Evaluation of the inflatable thermal blanket by skilled practitioners has resulted in general approbation: the opinion is that an inflatable thermal blanket efficiently and effectively treats hypothermia. However, while the prior art inflatable thermal blanket achieves its objective, certain improvements to it have been desirable in order to realize additional clinical objectives and to enjoy further advantages in its use during surgery. For example, the preferred use for an inflatable thermal blanket is patient temperature management, by which a patient's temperature is controlled by distributing thermally-controlled air over the patient's body. For this purpose, an inflatable thermal blanket is deployed to cover all, or a portion of, the patient's body; in addition, it may include means to access the patient, for surgery, while lying over the patient and providing temperature regulation. However, such coverage does not always provide a complete barrier between the surgical site and the patient.

A surgical drape is the usual means employed for provision of a barrier between a surgical site and other fields, during surgery. Relatedly, a surgical drape is employed for such purposes as keeping fluids confined to the surgical site, maintaining sterility of the surgical site, and screening the anesthesia work area. Attempts have been made to incorporate some functions of a surgical drape into certain elements of inflatable thermal blankets. One example of incorporation of barrier functions into an inflatable thermal blanket is found in U.S. Pat. No. 5,545,194, in which a portion of an inflatable thermal blanket is maintained, uninflated, while surgery is performed on a patient, and then is deployed and inflated over the surgical site. In U.S. Pat. No. 5,336,250, transparent uninflatable sheets at one end of an inflatable thermal blanket provide viewing of portions of a patient's body during medical treatment. In U.S. Pat. No. 5,300,101, plastic sheets with adhesive strips seal off a surgical site from a flow of warm air emitted by an inflatable thermal blanket.

One difficulty in providing access to a surgical site, or to other areas of a patient, during surgery, through an inflatable thermal blanket utilizing super-atmospheric, temperature controlled air is that the openings formed in the blanket to provide access may permit the temperature-regulated air to escape, thereby decreasing the thermal regulation achieved by use of the blanket.

Further, the draping functions achieved by the prior art uninflatable drapes that are provided as extensions of inflatable thermal blanket structures are limited. They are primarily used for localized entrapment of warmed air, and to limit sealing between the flow of warmed air and a surgical site. These are well short of all of the functions required of a surgical drape, Therefore, a need exists for a device that combines an inflatable thermal blanket that is capable of delivering a temperature controlled airflow to a patient in order to manage the patient's body temperature during surgery, while simultaneously providing a barrier between a surgical site and other areas and allowing access to the patient.

SUMMARY OF THE INVENTION

The invention improves the clinical usefulness of inflatable thermal blankets and surgical drapes during surgery by integrating them to provide a surgical barrier device that maintains patient temperature, while differentiating the surgical field from the remainder of the operating area.

Therefore the invention accomplishes the important objective of combining an inflatable thermal blanket with a surgical drape to permit a relatively unobstructed view of, and access to, a surgical site, while controlling patient temperature when in use.

A still further objective is to provide a surgical barrier device that incorporates an inflatable temperature control blanket, allowing surgical access to a surgical site that is sealed with respect to the super-atmospheric air within the blanket, and wherein the inflated blanket does not interfere with the surgical procedure.

The invention may be employed to provide numerous features which work together to allow surgical access to a patient while allowing the patient's temperature to be regulated. The invention also isolates the surgical site, while minimizing the risk that escaping air might contaminate the surgical site. The advantageous simplified structure of the surgical barrier device makes its production straightforward and economical.

The invention provides, in a "two-in-one" product, ease and convenience of use that greatly benefit the consumer.

BRIEF DESCRIPTION OF THE DRAWINGS

These and other important objectives and advantages will become evident when the detailed description of the preferred embodiments of the invention is read with reference to the below-summarized drawings, in which:

FIG. 10 is a perspective view of a first embodiment of a surgical barrier device constructed in accordance with the invention, with an inflatable structure for covering and thermally bathing the pelvic area and lower extremities of a patient, and a drape for covering additional portions of the patient's body, while providing medical access to the patient;

FIG. 11 is a diagrammatic plan view of the surgical barrier device of FIG. 10;

FIG. 12 is a perspective view of a second embodiment of a surgical barrier device constructed in accordance with the invention, for thermally bathing a patient using an inflatable cover for covering the chest and upper extremities of the patient and a drape for covering additional portions of the patient's body, while providing medical access to the patient;

FIG. 13 is a diagrammatic plan view of the surgical barrier device of FIG. 12;

DETAILED DESCRIPTION OF THE PREFERRED EMBODIMENTS

Figure 1:
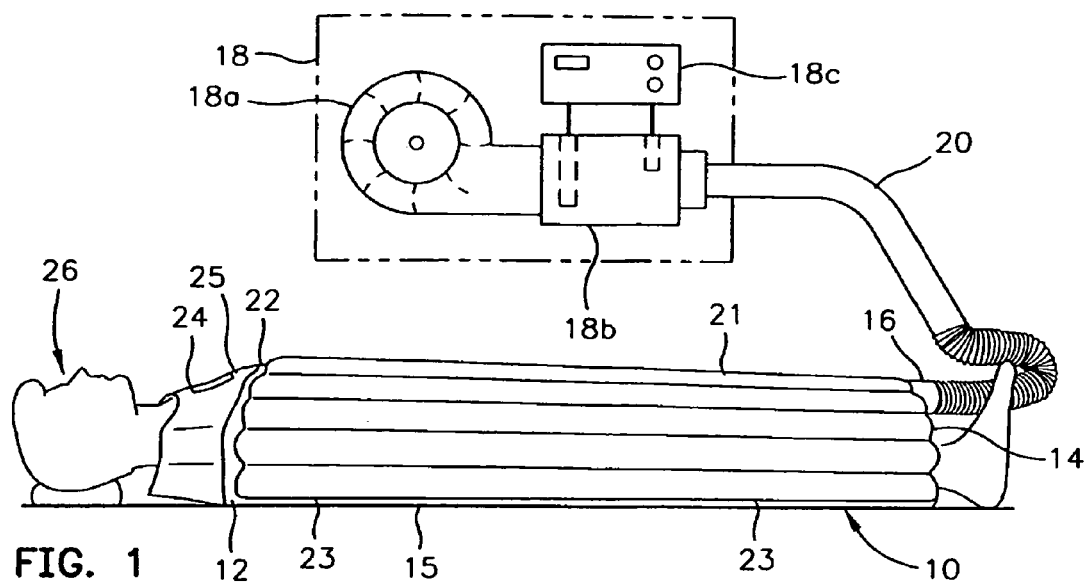
FIG. 1 is a side elevation view of an inflatable thermal blanket, with the blanket in use, and associated thermal apparatus indicated schematically.

This invention is described in preferred embodiments in the following description with reference to the Drawing Figures, in which like numbers represent the same or similar elements. While this invention is described in terms of the best mode for achieving the invention's objectives, it will be appreciated by those skilled in the art that variations may be accomplished in view of the teachings herein without deviating from the spirit or scope of the invention.

Inflatable Thermal Blankets When used herein, the term "inflatable thermal blanket" may be interchangeable with, but is not necessarily limited by, the term "airflow cover" used in U.S. Pat. No. 4,572,188. In this description, the term "inflatable thermal blanket" is meant to invoke an inflatable structure for delivering a thermally controlled inflating medium to space occupied by at least a portion of a patient's body when the inflatable thermal blanket is inflated. The purpose of the inflatable thermal blanket is to efficiently administer a uniformly thermally-controlled bath of the inflating medium to a patient within space beneath the blanket.

An inflatable thermal blanket is illustrated in FIG. 1. In FIG. 1, an inflatable thermal blanket 10 has a head end 12, a foot end 14 and two lateral edges, one indicated by 15. An inflation inlet cuff 16 is connected to a heater/blower assembly 18 having a compressor 18a, a heater 18b and a control unit 18c which may include user-selectable fan speeds, controllable heat amounts and temperature control. The heater/blower assembly 18 provides a stream of heated air through a connecting hose 20. When the heater/blower assembly 18 is operated, the stream of heated airflows through the inflation cuff 16. When the blanket is inflated, it displays a quilted upper surface 21. As described below, a pattern of apertures on the undersurface of the blanket (not shown in FIG. 1) convectively delivers the inflating heated air into the interior space enclosed by the inflated blanket.

The contour of the inflatable portion of the inflatable thermal blanket 10 may be varied at the head end 12 of the blanket to provide an uninflated blanket recess 22 in the quilted upper surface 21, which remains smooth and flat when the blanket is inflated. Circulation of the heated air is accelerated through the inflatable thermal blanket by exhaust port openings in the upper surface, adjacent the lateral edges of the blanket. Two exhaust port openings are indicated by reference numeral 23. Further, a bib 24 made of an absorbent material is attached to the head end 12 of the inflatable thermal blanket in the vicinity of the uninflated recess 22. In fact, as shown in FIG. 1, the bib 24 includes a semi-circular tab 25 that extends into the recess 22.

As illustrated in FIG. 1, the inflatable thermal blanket of the invention is inflated and bathes a patient 26 with the thermally-controlled air used to inflate the blanket. While the patient is being thermally bathed, the uninflated recess 22 permits observation of the patient's head, face, neck, and chest from almost any location with respect to the inflatable thermal blanket 10. Thus, if the patient is placed on a gurney or a bed, the head of which is against a wall, a care giver such as a nurse, intern, resident, or doctor, can keep the patient's face under observation from the foot end 14 of the inflatable thermal blanket 10. Respiration can be detected by the rise and fall of the bib 24 and the uninflated area 22, which form an uninflated drape that rests directly on the patient's chest. Moreover, the bib 24 will provide an absorbent sink for stray, unconfined liquids in the area of the patient's head or at the head end 12 of the inflatable thermal blanket 10.

Figure 2:
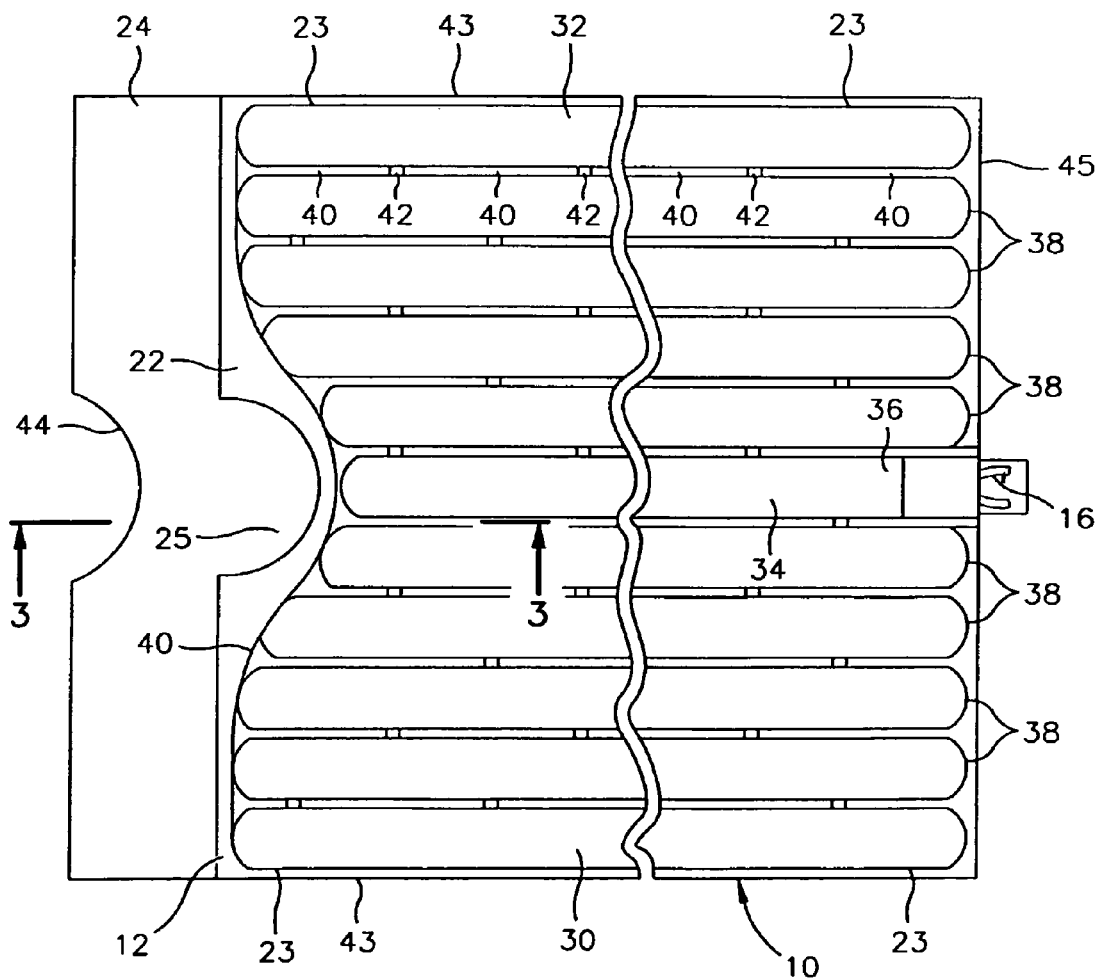
FIG. 2 is an enlarged top plan view of the inflatable thermal blanket of FIG. 1, opened flat.

FIG. 2 is a plan view of the inflatable thermal blanket 10 opened flat to show details of its structure. FIG. 2 illustrates the upper surface of the inflatable thermal blanket, that is, the side that is visible in FIG. 1. As seen, the upper surface consists of a parallel array of elongated tubes of which 30 and 32 are the lateral most tubes, 34 is the center tube, and the tubes 38 are arrayed between one of the lateral most tubes and the center tube. Each tube is separated from an adjacent tube by a discontinuous seam, one of which is indicated by 40. The seam 40 separates the tube 32 and its nearest adjacent neighbor 38. The discontinuous seam 40 is interrupted by passageways 42 communicating between the tubes. An interrupted seam separates every tube from one adjacent neighboring tube. The seams permit the inflatable thermal blanket, when inflated, to assume a tubular structure on the upper surface, while the ports 42 permit full circulation of the inflating medium throughout the array of tubes. The foot-end seam 45 is continuous. The tubes are inflated through the center tube 34 which transitions to a port 36, through which the inflation cuff 16 is inserted. The edge seams 43 are discontinuous only at the exhaust port opening locations 23. A seal can be made between the inflation port 36 and the inflation cuff 16 by any conventional means, for example, an o-ring, or even tape. When the inflating medium is introduced into the center tube 34, it flows laterally from the center tube into all of the other tubes through the ports 42. Near the head end 12, a continuous seam 40 defines the forward end of all of the tubes, with the seam assuming a bell curve shape. On the head end side of the seam 40, the inflatable thermal blanket 10 is uninflatable. The bell-shaped seam 40 thus defines the uninflated recess area 22 at the head end of the inflatable thermal blanket 10, which is essentially coplanar with, or substantially parallel to, the underside of the blanket. As shown in FIG. 1, by virtue of its structural integration with the rest of the inflatable thermal blanket 10, the uninflated recess 22 forms an uninflatable drape that extends over the upper chest of the patient 26 when the blanket is inflated. This helps to thermally bathe the patient while preventing the migration of air from inside the blanket 10 to the patient's head and neck area. Because the recess 22 is uninflated, it provides a wide-angled viewing gap in the inflated contour of the upper surface 21. The gap is filled by continuation of the underside of the blanket. It is also noted that the pattern of inflatable tubes can be replaced by other suitable patterns. The tubes are preferred since they impart strength and shape to the inflated structure; other inflatable structures are contemplated, however.

The absorbent bib has an indent 44 cut into its outside edge, which permits the blanket to be drawn up to the chin of a patient and which provides absorbency laterally up the neck of the patient. The absorbent bib can consist of any absorbent material such as a single- or multi-ply tissue paper which is used to make paper towels.

Figure 3:
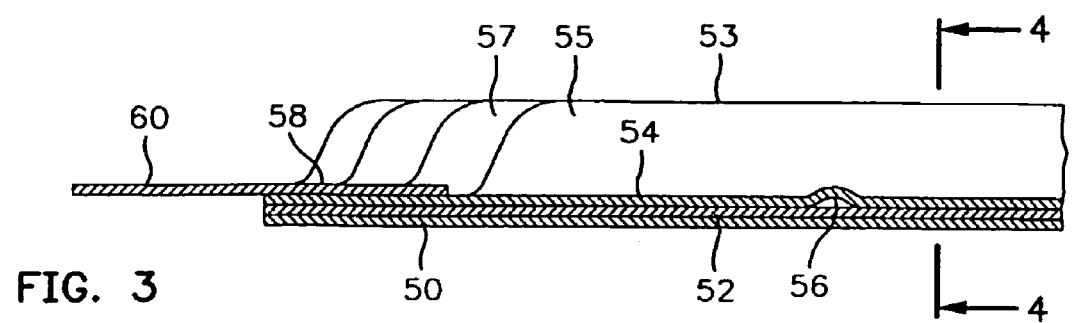
FIG. 3 is an enlarged sectional view taken along line 3-3 of FIG. 2.
Figure 4:
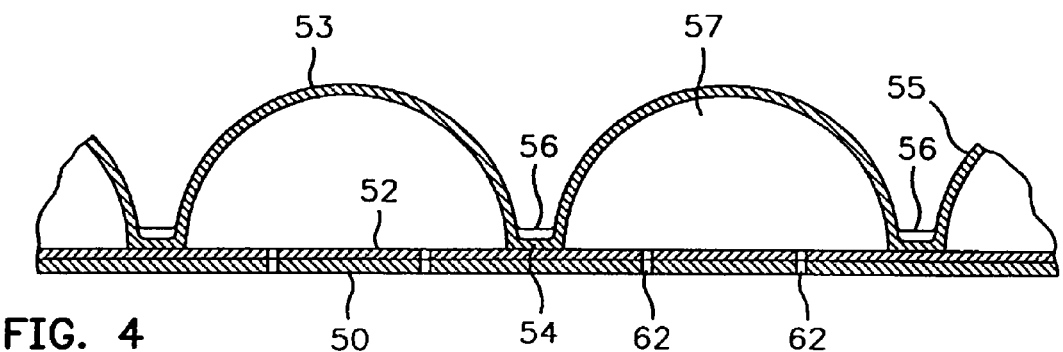
FIG. 4 is a further enlarged sectional view taken along line 4-4 of FIG. 3.

Construction details of the inflatable thermal blanket 10 are illustrated in FIGS. 3 and 4. The inflatable thermal blanket 10 is assembled from a base sheet and a top sheet. The base sheet consists of an underside layer 50 formed from a flexible, fibrous, preferably non-woven structure composed of synthetic or natural materials capable of bonding to an upper side layer 52 of a heat-sealable synthetic material such as plastic. For example, the underside layer 50 may be a non-woven, hydroentangled polyester material and the upper side layer 52 may include a polypropylene film which is extrusion-coated onto the polyester layer 50. Alternatively, the underside layer 50 may comprise a non-woven, paper-based material to which the upperside layer 52, including either a polyethylene or polypropylene film, has been glue laminated.

In one exemplary embodiment of the layers 50 and 52, a stratum of absorbent tissue paper prelaminated with a layer of heat-sealable plastic has been used. Material of such construction is commercially available in production rolls and is used to make painter's drop cloths.

The top sheet 53 of the inflatable thermal blanket preferably comprises the same material as the upperside layer 52 of the base sheet. The top sheet 53 thus may consist of a sheet of plastic bonded to the plastic upperside 52 of the base sheet. It is preferably attached by a continuously-running web process including stations that provide an interruptible heat-sealing process. This interruptible heat sealing process can be controlled to form elongate heat seals that define the inflatable tubes therebetween. The seals can be formed as continuous air impervious seals or discontinuous air permeable seals. The interruptible heat sealing process is used to form the continuous seams, one of which is the bell-shaped seam 40 in FIG. 2, the interrupted seams, one of which is indicated by 54, and the inflatable tubes, one of which is indicated by 55. As can be seen in FIG. 3, the interruption of the seam 54 forms a passageway 56 between adjacent tubes 55 and 57.

The absorbent bib and tab are shown in FIG. 3 as a single material layer 60/58. This layer may comprise an uninflatable extension of the blanket structure formed by the single continuous seal between upper and base sheets. Alternatively, they may be formed from separate material sheets cut to the outlines illustrated in FIG. 2. The absorbent material forming the bib and tab can be bonded to the upper plastic layer by heat processing or by gluing.

Deletion of the bib and tab is also contemplated. In that instance, the inflatable thermal blanket would still have the viewing recess, which would be defined by the continuous seam at the head end, and which would be filled with the forward portion of the base sheet.

Returning to FIG. 2, circulation of heated air through the blanket may be aided by exhaust port openings 23, which either open through the upper plastic sheet, which is heat sealed to the base of the blanket, or through the edge seams 43 between the upper plastic sheet and base sheet. The openings 23 vent the heated inflating air out of the outermost tubes 30 and 32, away from the underside of the blanket. Because air can circulate to, and through, the blanket edges, the inflating air in the outermost tubes is hotter than if the openings were absent. This results in hotter air being delivered through the underside apertures toward the edge of the blanket.

The exhaust port openings may comprise slits in the edge seams 43 of the inflatable thermal blanket that vary in length from 1¾ to 2 inches. Each edge seam 43 may be discontinuous approximately at each corner of the blanket so that inflating air is vented away from the underside of the inflated blanket. This keeps the relatively "colder" air at the blanket edges from mixing with relatively "hotter" air exhausted into the structure through the underside apertures. The result is a "flatter" temperature profile of air within the blanket than without the vents, which raises the average temperature within the inflated structure and makes the temperature distribution in the structure more uniform. Resultantly, the clinical effect of the blanket is enhanced. Heating is better controlled, and more uniform, with greater comfort to the patient.

Figure 5:
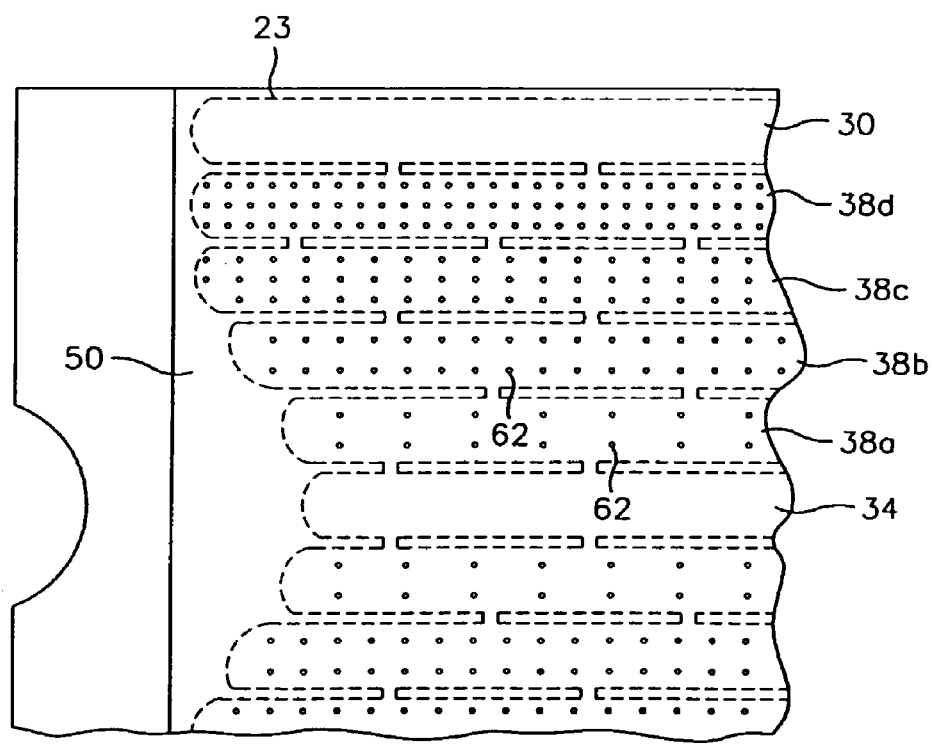
FIG. 5 is a partial underside view of the inflatable thermal blanket of FIG. 1.

The inflatable thermal blanket is enabled to bathe a patient in the thermally controlled inflating medium introduced into the inflatable thermal blanket, when inflated, by means of a plurality of apertures 62 shown in FIGS. 4 and 5. The apertures extend through the underside of the blanket, which includes the layers 50 and 52. The apertures 62 are made in the footprints of the tubes of the blanket upper side according to a pattern which has been determined to deliver a very uniform thermal bath. In this regard, no apertures are provided through the underside into the lateral most tubes 30 and 32, or into the center tube 34. In addition, the apertures 62 are provided through the underside to the apertured tubes in a density which varies inversely with the proximity of the tube to the center tube 34. Thus, the hole density increases from the tube 38a through the tube 38d. Even with the exhaust port openings, the temperature of the inflating medium exhibits a drop from the center to the lateral most tubes. The varying density of the apertures 62 tends to reduce this gradient further by forcing hotter air to the edges of the blanket. Thus, the thermal bath delivered to the patient is of a generally uniform temperature. The aperture density variation also equalizes the flow of inflating medium out of the apertures. As will be evident, the inflating pressure will be greatest at the center tube 34 and will tend to diminish toward the lateral edges of the inflatable thermal blanket. Therefore, fewer apertures are required for the tubes near the center tube 34 to deliver the same amount of air as the relatively greater number of apertures in the tubes at a greater distance from the center tube 34. The apertures comprise openings which can be of any appropriate shape.

Figure 6:
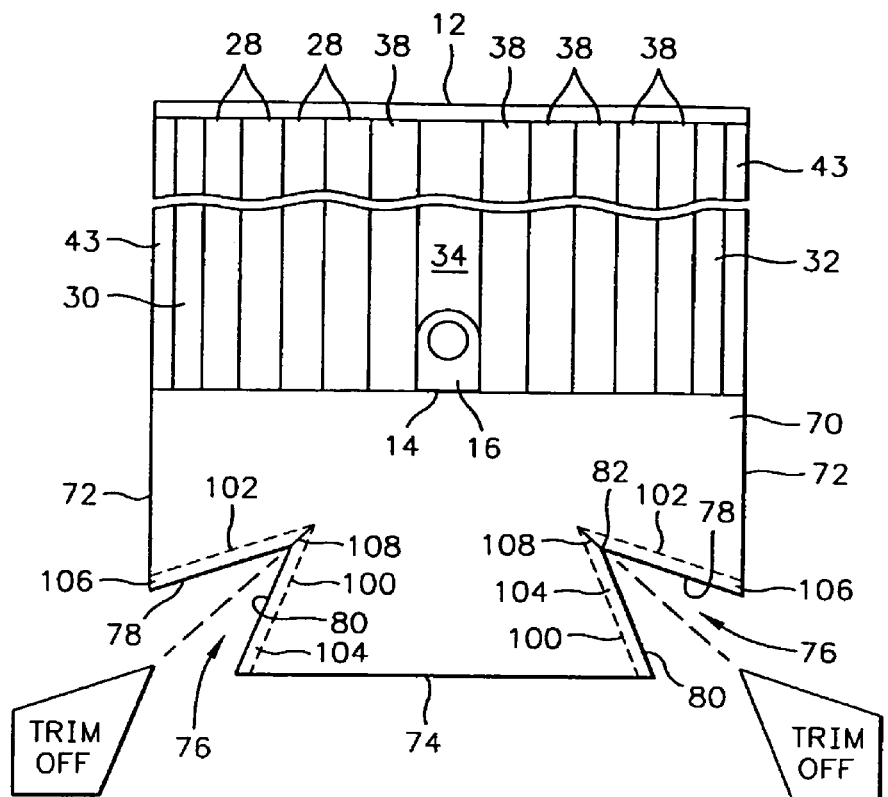
FIG. 6 is a partial diagrammatic top plan view of an inflatable thermal blanket that includes a partially constructed drape.
Figure 7:
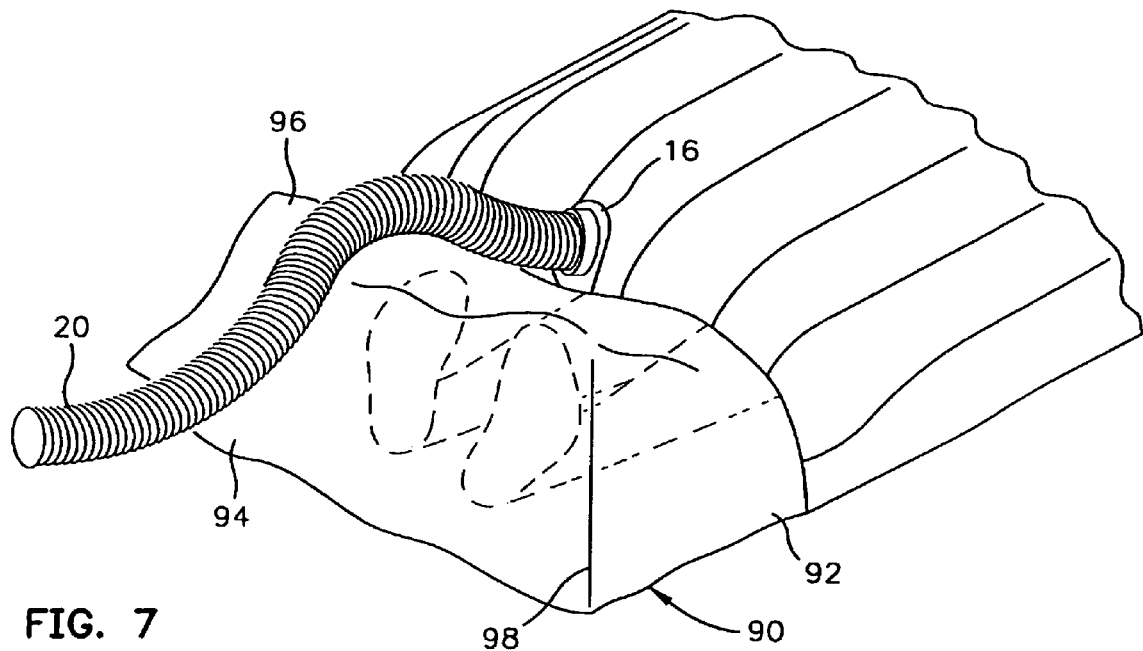
FIG. 7 is a partial projected view of the fully constructed inflatable thermal blanket of FIG. 6 in use, with the patient's feet illustrated by hidden lines underlying the foot drape.

An inflatable thermal blanket including a foot drape is illustrated in FIGS. 6 and 7. The foot end 14 of the inflatable thermal blanket 10 is modified to provide an uninflatable drape-forming section 70 formed by a rearward extension of the base sheet 50/52 and an uninflatable portion of the heat-sealable plastic top sheet bonded to the base sheet. The drape forming sheet 70 has sides 72 extending parallel to and rearwardly from the outside edge of the edge seams 43, and a rear edge 74. Optionally, the drape-forming sheet 70 further includes a pair of V-shaped cuts 76 in the rear corners thereof. The V-shaped cuts 76 are formed by converging cuts 78 and 80, extending inwardly from one of the sides 72 and the rear edge 74, respectively, to a point of intersection 82. As shown in FIG. 7, the drape-forming section 70 may be formed into an uninflatable foot drape 90 that includes a pair of side portions 92, a rear portion 94 and an upper portion 96. The drape 90 is so formed by joining the edges 78 and 80 of the V-shaped cuts 76 to form a pair of seams 98. To form the seams 98, the V-shaped cut edges 78 and 80 may be folded about respective lines 100 and 102 that parallel the edges 78 and 80, as shown in FIG. 6. The resulting respective folded surfaces 104 and 106 may then be fastened together by appropriate means such as heat sealing. Joining the surfaces 104 and 106 forms a crease 108 and transforms the two dimensional drape forming section 70 into the three dimensional drape 90.

The resultant drape 90 is uninflatable and traps and retains heat under the thermal blanket around the patient's feet, to warm the feet. As shown in FIG. 7, the drape 90 also insulates the bare skin of the feet from excessive conductive heat from the inflating hose 20 in the event the hose is oriented in a position wherein it might otherwise come in contact with the feet. Patient warming and comfort is thus further enhanced.

Figure 8:
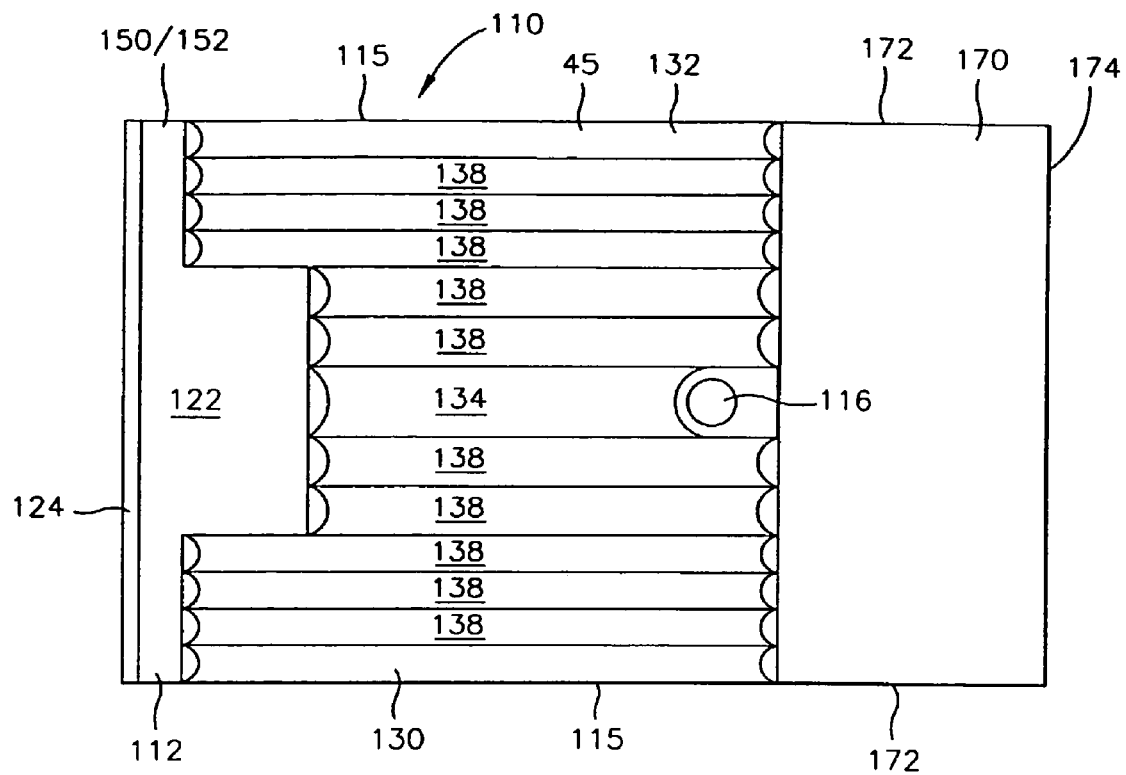
FIG. 8 is a top plan view of a partially constructed thermal blanket for thermally covering the pelvic area and lower extremities of a patient.
Figure 9:
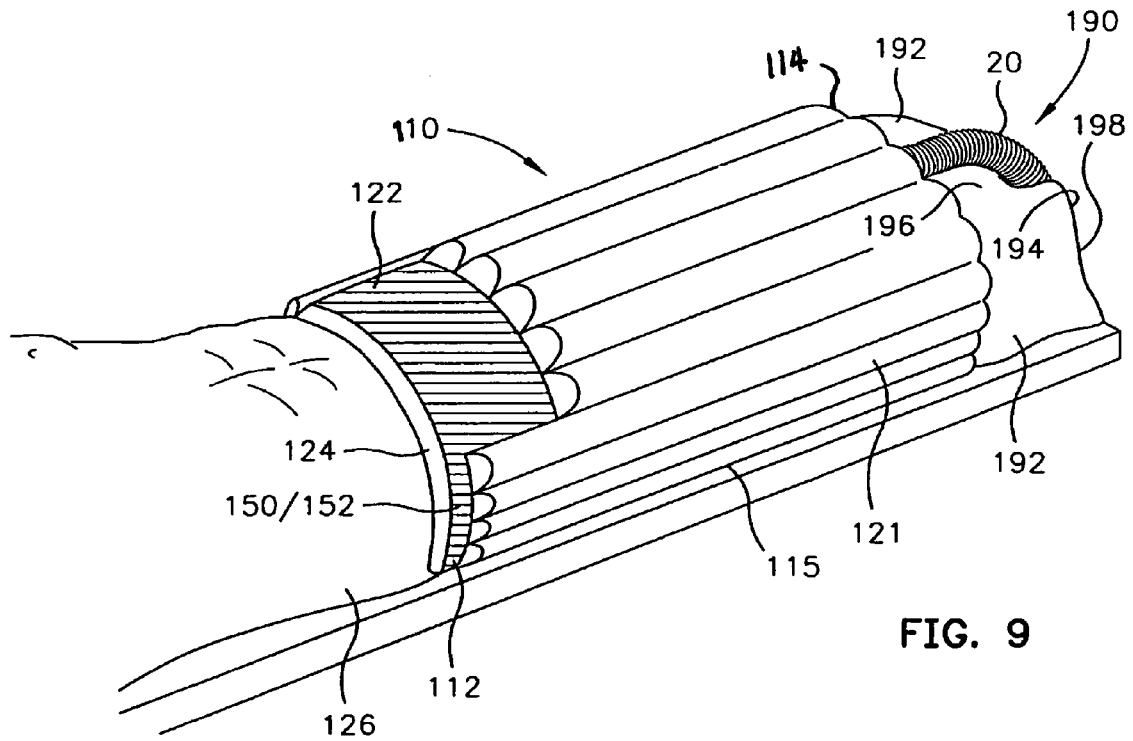
FIG. 9 is a partial projected view of the fully constructed inflatable thermal blanket of FIG. 8 in use.

An inflatable lower body covering with a foot drape is illustrated in FIGS. 8 and 9. This covering warms convectively by exhausting warm air onto a patient. The thermal covering in this case is similar to the covering shown in FIGS. 6 and 7, except that the covering may be shortened to cover only the pelvic area and lower extremities of the patient. Moreover, the head end of the covering may be modified to provide an open flat working area for the placement of instrumentation and to improve visualization of the care site, as shown in FIG. 9. As in the case of the thermal coverings discussed above, the covering 110 of FIGS. 8 and 9 includes a head end 112, a foot end 114, a pair of lateral edges 115, and an inflation inlet cuff 116 which may be connected through a heater tube 20 to a heater/blower assembly such as the assembly 18 shown in FIG. 1. As shown in FIG. 9, the covering 110, when inflated, has a quilted upper surface 121. Like the thermal covering 10, a pattern of apertures on the undersurface of the blanket 110 convectively delivers the inflating heated air into the interior space enclosed by the inflated thermal blanket.

At the head end of the quilted upper surface 121, an uninflated blanket recess 122 is formed to provide an open flat working area for the placement of instrumentation, and to improve visualization of a care site on the patient's torso. Alternatively, the head end of the quilted upper surface 121 could extend directly from one edge 115 to the other edge 115 without the provision of the uninflated blanket recess 122. Further, an adhesive strip 124 made of an adhesive material may be attached to the head end 112 of the covering 110 and extend between the edges 115. The adhesive strip 124 is mounted with its adhesive side oriented toward the base sheet, which includes an underside layer 150 formed from a flexible material capable of bonding to a layer 152 of heat sealable plastic. The layers 150/152 are formed in the same manner as the layers 50/52 shown in FIG. 3 and described above. Mounted to the underside of the adhesive strip 124 is a backing strip, which may be positioned partially between the adhesive strip 124 and the layer 152 to prevent inadvertent peel-off.

As shown in FIG. 9, the adhesive strip 124 may be adhered above the patient's pelvic and groin area to securely position the uninflated recess 122 so that it acts as a drape to thermally bathe the patient and prevent the migration of air from inside the covering 110 to the care site. Moreover, the optional uninflated recess 122 may be large and well-defined in order to improve visualization of the operating field and provide sufficient working area for resting instruments or other items during the rendering of care to a patient 126.

Like its counterpart covering 10, the covering 110 may include a parallel array of elongated tubes of which 130 and 132 are the lateral most tubes, 134 is the center tube, and the tubes 138 are arrayed between one of the lateral most tubes and the center tube. The thermal covering 110 further includes a uninflated foot drape for retaining a thermal medium around a patient's feet. As in the covering shown in FIG. 6, the covering 110 is provided with an uninflated drape forming section 170 extending rearwardly from the foot end 114. The drape forming section 170 includes a pair of sides 172 and a rear edge 174. As shown in FIG. 9, the drape forming section 170 may be formed into an uninflatable foot drape 190 that includes a pair of side portions 192, a rear portion 194, and an upper portion 196.

As with the longer full-body inflatable thermal blanket of FIGS. 1 and 2, the covering 110 may be provided without a foot drape as appropriate. In that case, it may be desirable to slidably mount a protective sleeve over the heater tube 20 to prevent the tube from contacting the patient.

Advantageously, it will be observed that the lower body warming cover 110 maintains a thermal medium around the pelvic and groin area and lower extremities of the patient, while at the same time exposing the patient's torso and head as may be necessary for the provision of medical care and treatment to those areas.

The Invention: The invention is a surgical barrier device that includes an inflatable thermal blanket for deployment over a portion, or portions, and/or a limb, or limbs, of a patient, and a surgical drape for isolating a surgical site, covering additional portions and/or limbs of the patient, and providing access at the surgical site.

FIGS. 10 and 11 show a first embodiment of the surgical barrier device, in which the inflatable thermal blanket is deployed over the pelvic area and lower extremities of the patient. In FIG. 10, a patient 300 reclines on an examination table 302. The patient's head 304 lies prone on the table 302, as do the patient's torso 306, arms 308, legs 310, and feet 312. The patient's arms 308 lie at the patient's side and the patient's feet 312 are slightly apart. A surgical barrier device 319 includes an inflatable thermal blanket 320, constructed to warm convectively by exhausting warm air onto the patient 300, and a surgical drape 321 constructed to provide a barrier between a surgical site on a patient's body and the remainder of the patient's body. The inflatable thermal blanket 320 is configured to cover the patient's pelvic area and lower extremities, while the drape 321 provides barrier functions, in addition to covering additional portions of the patient and providing access to a surgical site. The surgical barrier device 319 includes two ends 322, and 324, a pair of outer lateral edges, or sides, 326 and 327, and an inflation inlet cuff 328 that opens into the inflatable thermal blanket 320. The inlet cuff 328 may be connected through a flexible heater hose, such as the tube 20 shown in FIG. 1, to a heater/blower assembly such as the assembly 18 shown in FIG. 1. In FIG. 10, the inlet cuff 328 is shown mounted on the underside of the inflatable thermal blanket 320, but it could also be mounted on the upperside of the blanket.

Elongate extensions 330 and 332 at one end of the inflatable thermal blanket 320 define a recess 334 therein. The recess 334 provides an area for viewing and accessing a surgical site in the abdomen and lower chest area of the patient.

Figure 18:
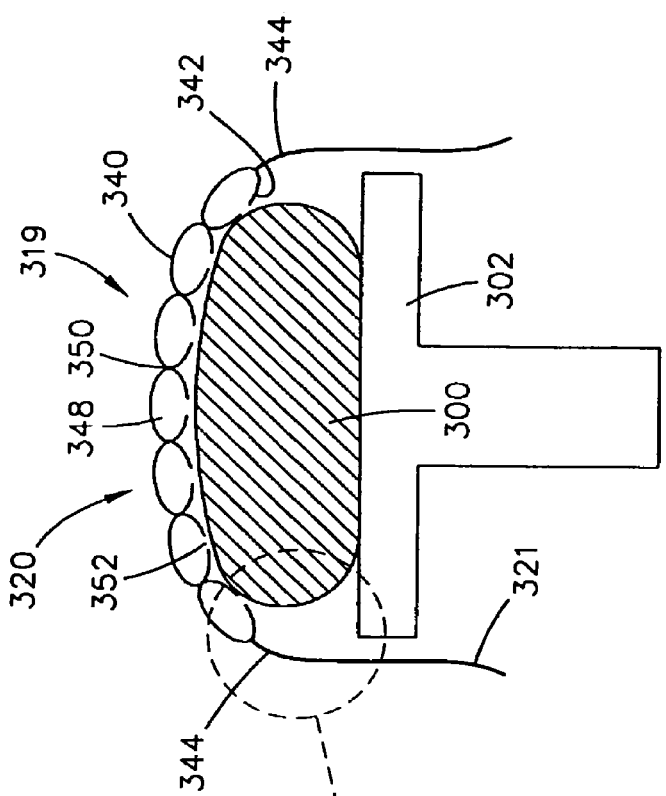
FIG. 18 is a diagrammatic cross sectional view of an inflatable thermal blanket in accordance with the first through fourth embodiments of the invention showing a first construction embodiment thereof.
Figure 19:
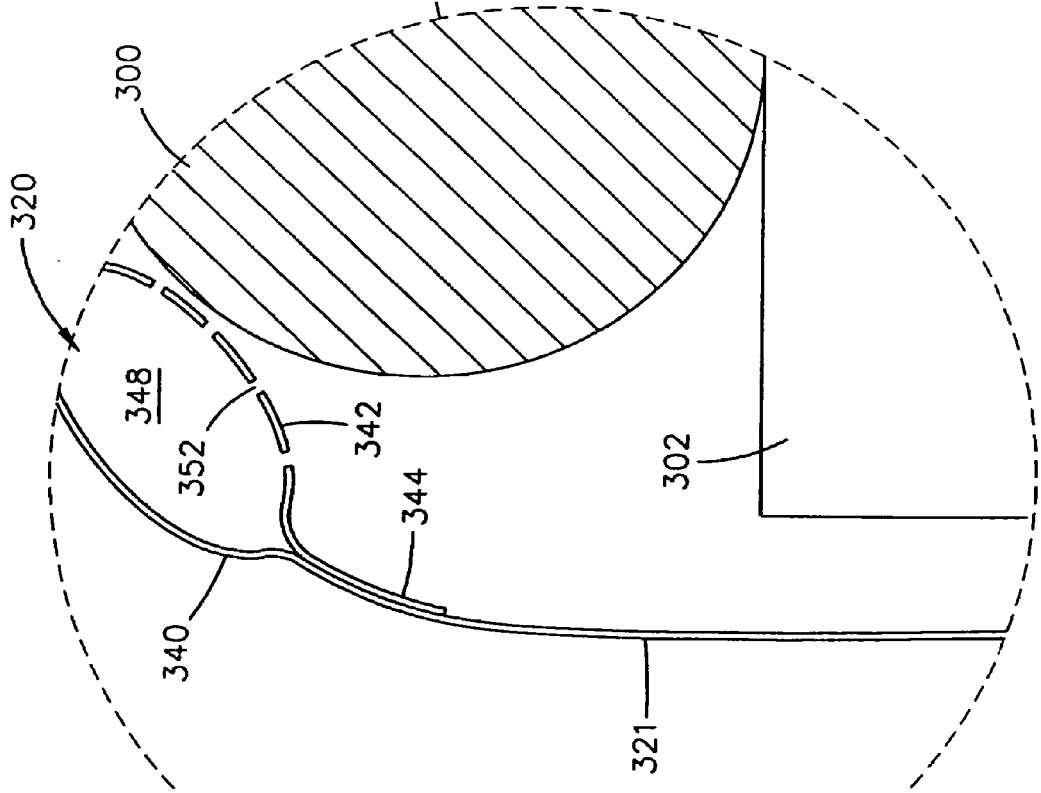
FIG. 19 is an enlargement of a portion of the surgical barrier device of FIG. 18.

The inflatable thermal blanket 320 is formed as an inflatable covering that includes a flexible upper sheet 340 and a flexible base sheet 342, as shown in FIGS. 18 and 19. These sheets are secured to each other along a peripheral seam 344 that extends around the periphery of the inflatable thermal blanket. The peripheral seam 344 can be formed by a heat sealing process, as described above. It is preferably continuous, but may also be formed with interruptions at selected locations thereof to facilitate egress of the inflating medium, e.g., heated air, for the purposes described above. The upper sheet 340 and the base sheet 342 are constructed using the materials and techniques described above in connection with FIGS. 2-4, forming a parallel array of elongated tubes using seams formed by elongated heat seals as shown in FIGS. 1-4, or an array of quasi-discrete inflatable spaces 348 formed using point seals 350, as shown in FIGS. 10 and 11. As FIGS. 18 and 19 show, a plurality of apertures 352 (identical to the apertures 62 shown in FIG. 5) open through the base sheet 342 into the inflatable thermal blanket 320. The apertures convectively deliver the inflating medium into the space surrounding the patient, which is enclosed by the surgical barrier device 319. The base sheet 342 of the inflatable thermal blanket 320 is preferably constructed like the base sheet of FIG. 3, which comprises an underside layer 50 made from a flexible, fibrous material, and an upperside layer 52 made from a heat-sealable synthetic material. The apertures may be formed as holes extending through both of the layers 50 and 52 of this base sheet. Alternatively, the apertures may be formed as holes extending through the upper layer 52 of the base sheet, and as spaces which naturally occur between the fibers of the fibrous material used to form the underside layer 50.

Returning to FIGS. 10 and 11, the surgical drape 321 is attached to, or integrally formed with, the inflatable thermal blanket 320. The drape 321 extends from the periphery of the inflatable thermal blanket 320, including the recess 334, and extends outwardly to define the ends 322 and 324 and the sides 326 and 327 of the surgical barrier device 319. As shown in FIG. 11, the drape 321 is generally rectangular in shape. It is preferably sized so that it extends over the entire upper surface of the table 302, so as to completely cover the patient 300. As such, the end 322 extends at least to cover the patient's head, the end 324 extends at least to cover the patient's feet, and the sides 326 and 327 extend at least to cover the patient's sides, arms and legs. More preferably, the drape 321, at the foot end 324 and sides 326 and 327, hangs well below the edge of the table 302.

In order to provide access to the patient 300 for performing surgery at a surgical site 362, the drape 321 is formed with a cutout or window 364. An attachment device 366, such as one or more adhesive strips, may be provided around the edge of the cutout 364 in order to secure the drape 321 to the patient and to provide a seal that isolates the surgical site and keeps the inflating medium away from it. Because the drape 321 is not inflatable, it may be pressed flush against the patient 300 around the periphery of the cutout 364, and optionally secured, so that unobstructed access to the patient is ensured.

The drape 321 is employed for the same purposes as surgical drapes that are known in the art. The drape 321 also helps retain the inflating medium proximate to the patient body, after it has been exhausted from the blanket 320 through apertures in the base sheet thereof. Air that is exhausted from the inflatable thermal blanket 320 flows beyond the edge thereof and beneath the drape 321, where it is maintained in proximity to the patient 300. At the head end 322, it is necessary to keep the drape 321 away from the patient's nose and mouth, so that respiration is not impaired. For that purpose, a frame structure, which may be formed by a pair of vertical posts 368 mounted on the table 302, is provided. The head end 322 of the surgical barrier structure 319 may be wrapped around the posts 368 and secured using tape 370 or any other appropriate fastening device, such as clips, etc.

Figure 20:
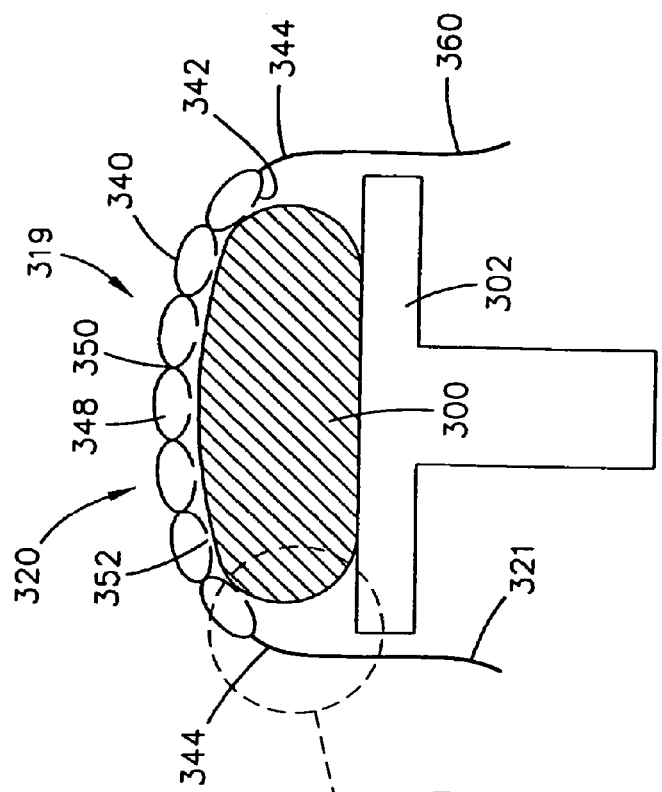
FIG. 20 is a diagrammatic cross sectional view of a surgical barrier device in accordance with the first through fourth embodiments of the invention showing a second construction embodiment thereof.
Figure 21:
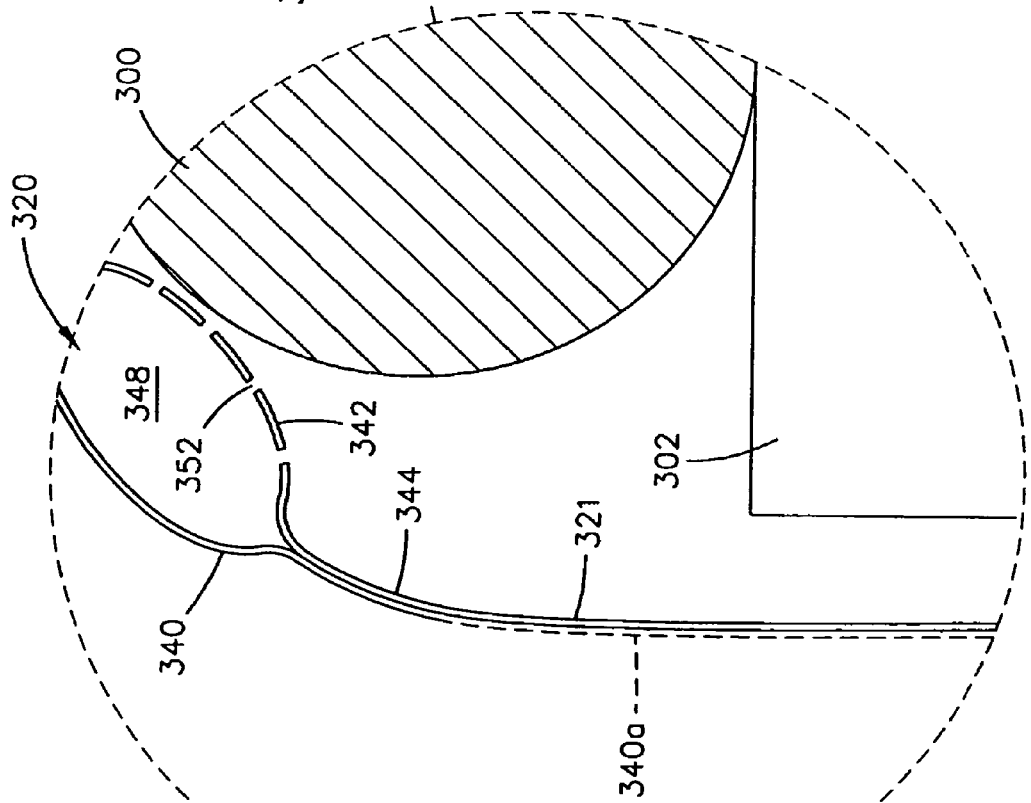
FIG. 21 is an enlargement of a portion of the surgical barrier device of FIG. 20.

The drape 321 can be formed in a variety of ways. As shown in FIGS. 18 and 19, the drape 321 can be formed as an extension of the material forming the upper sheet 340 of the inflatable thermal blanket 320. Alternatively, as shown in FIGS. 20 and 21, the drape 321 can be formed as an extension of the material forming the base sheet 342 of the inflatable thermal blanket 320. The drape 321 can also be formed as an extension of both of the aforementioned sheets 340 and 342. This is shown by the dotted line 340a, which represents extension of the upper sheet 340, if desired. In these embodiments, the drape 321 is formed integrally with the inflatable thermal blanket 320.

Figure 22:
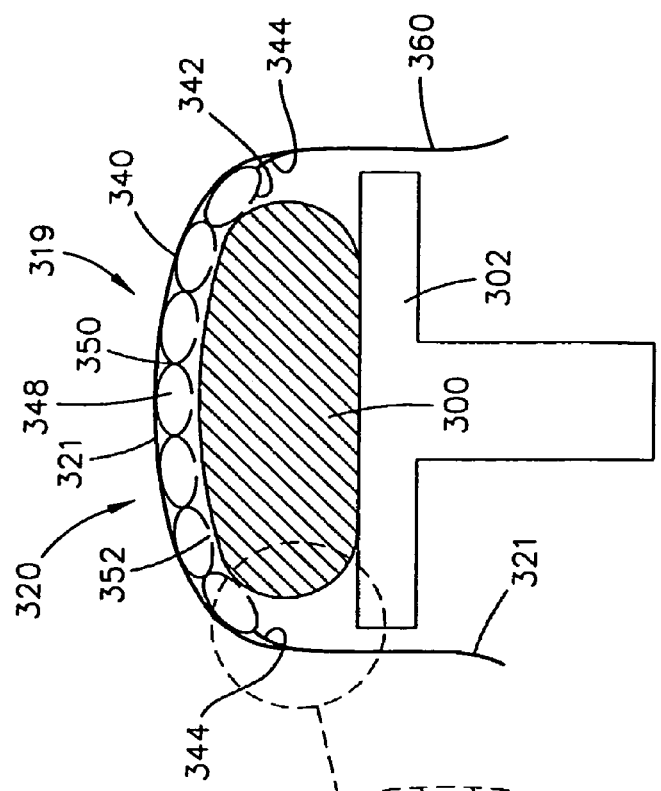
FIG. 22 is a diagrammatic cross sectional view of a surgical barrier device in accordance with the first through fourth embodiments of the invention showing a third construction embodiment thereof.
Figure 23:
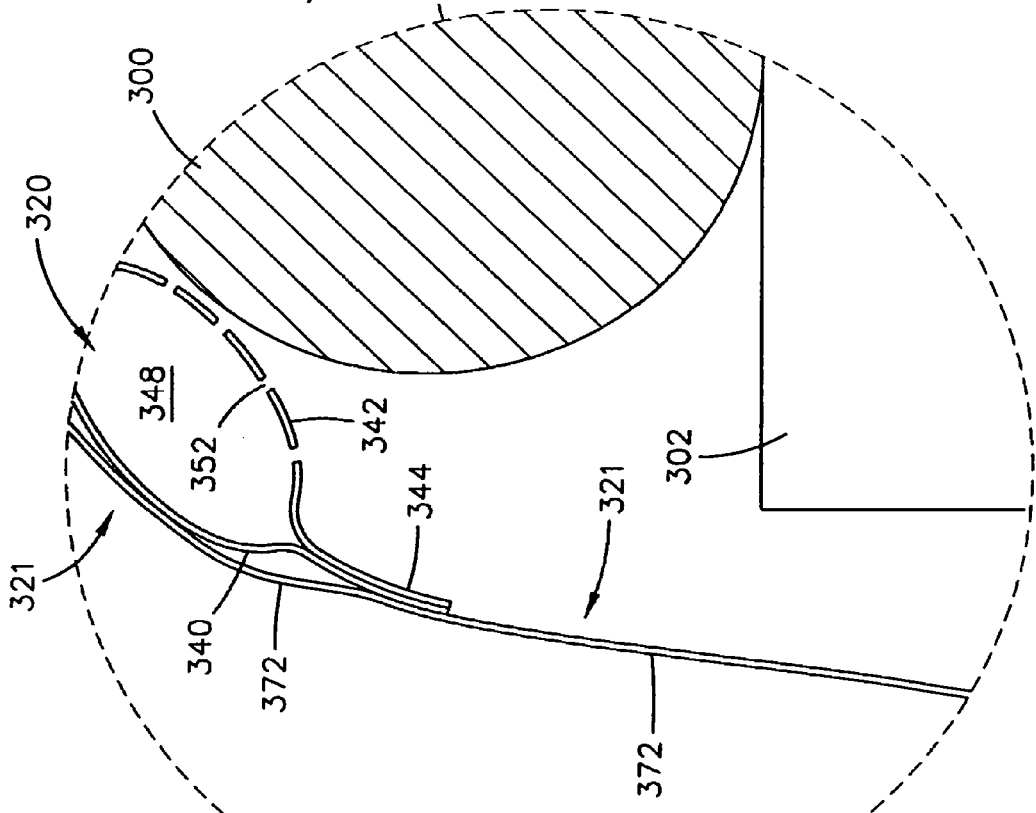
FIG. 23 is an enlargement of a portion of the surgical barrier device of FIG. 22.

Alternatively, as shown in FIGS. 22 and 23, the drape 321 can be formed as one or more separate sheets of material 372 that are attached by heat sealing, gluing, welding or the like, around the periphery of the upper sheet 340 (or the base sheet 342) at the location of the edge seam 344. Each sheet 372 may be configured as fringe sheet that is attached at an edge portion thereof to the upper sheet 340 (or the base sheet 342). More preferably, however, one or more single large sheets may be placed over and attached to the top of the upper sheet 340.

As shown in FIG. 10, the inflatable thermal blanket 320 is inflated during use with the inflating medium. When inflated, the inflatable thermal blanket 320 is positioned over the patient's pelvic region and lower extremities. The drape 321 advantageously covers the patient 300 and hangs downwardly along the sides and foot end of the table 302 to help retain the inflating medium on the patient, away from the surgical site. Preferably, the attachment device is operated to attach the drape 321 to the patient, around the surgical site, thereby to perform the desired barrier functions of a surgical drape, and to provide access to the surgical site 362.

FIGS. 12 and 13 illustrate a second embodiment of the surgical barrier device 419 for use in abdominal surgery, in which an inflatable thermal blanket 420 is deployed for thermally bathing the chest and upper extremities of a patient, and a surgical drape 421 is deployed for covering additional portions of the patient's body, while performing barrier functions and providing access to a surgical site in the patient's abdomen and lower chest area.

In FIG. 12, a patient 400 is reclined on an examination table 402. The patient's head 404 lies prone on the table 402, as do the patient's torso 406, arms 408, legs 410 and feet 412. The patient's feet 412 are slightly apart. The patient's arms 408 are spread apart laterally at approximate right angles to the patient 400 and are supported on lateral arm rests 414 that are attached to the table 402. The surgical barrier device 419 (that includes the inflatable thermal blanket 420 and the surgical drape 421) is deployed over the patient. The thermal blanket 420 is constructed to convectively warm by exhausting warm air onto the patient 400. The inflatable thermal blanket 420 is similar in most respects to the inflatable thermal blankets shown in the preceding embodiments, except that it is configured to have an inflatable portion that extends over the patient's chest and upper extremities, while the surgical drape 421 covers additional portions of the patient. As in the case of the embodiment disclosed above, the surgical barrier device 419 includes ends 422 and 424. The surgical barrier device 419 has an extended arm portion such that there are upper and lower pairs of outer lateral edges or sides, indicated by 426a and 427a, and 426b and 427b, respectively, and an inflation inlet cuff 428 that opens into the inflatable thermal blanket 420. The inlet cuff 428 may be connected through a flexible heater hose, such as the heater tube 20, to the heater/blower assembly 18, the construction of which is described above in connection with FIG. 1. In FIG. 12, the inlet cuff 428 is shown mounted to the underside of the blanket 420, but it could also be mounted to the upperside of the blanket.

The inflatable thermal blanket 420 is elongated at 430 and 432 so as to traverse substantially all of the patient's arms 408 as they lie on the arm rests 414 of the table 402. A pair of upper and lower central recesses 434 and 436 are formed in the inflatable thermal blanket 420. The upper recess 434 provides an area for viewing the patient's head 404. The lower recess 436 provides an area for viewing a care site.

The inflatable thermal blanket 420 is formed as an inflatable covering that includes a flexible upper sheet and a flexible base sheet that are identical to the upper and base sheets 340 and 342 shown in FIGS. 18 and 19. These sheets are secured to each other along a peripheral seam 444 that extends around the periphery of the inflatable portion. The peripheral seam 444 can be formed by a heat sealing process as described above. It is preferably continuous, but may also be formed with interruptions at selected locations thereof to facilitate egress of the inflating medium, e.g., heated air, as described above. The upper and base sheets of the inflatable thermal blanket 420 are constructed using the materials and techniques described above in connection with FIGS. 2-4, forming a parallel array of elongated tubes using seams formed by elongated heat seals as shown in FIGS. 1-4, or an array of quasi-discrete inflatable chambers 448 formed using point seals 450, as shown in FIGS. 12 and 13. A plurality of apertures identical to the apertures 352 shown in FIGS. 18 and 19 open through the base sheet into the inflatable thermal blanket 420. The apertures convectively deliver the inflating medium into space surrounding the patient, which is enclosed by the surgical barrier device 419. The base sheet of the inflatable thermal blanket 420 is preferably constructed like the base sheet of FIG. 3, which comprises an underside layer 50 made from a flexible, fibrous material, and an upperside layer 52 made from a heat-sealable synthetic material. The apertures may be formed as holes extending through both of the layers 50 and 52 of this base sheet. Alternatively, the apertures may be formed as holes extending through the upper layer 52, and as spaces which naturally occur between the fibers of the fibrous material used to form the underside layer 50.

The surgical drape 421 is attached to, or formed integrally with, the inflatable thermal blanket 420. The drape 421 extends from the periphery of the inflatable thermal blanket 420, including the recesses 434 and 436, and extends outwardly to define the head end 422, the foot end 424, the lower sides 426a and 427a, and the upper sides 426b and 427b of the surgical barrier device 419. As shown in FIG. 13, the drape 421 is T-shaped in order to cover the patient's arms 408. It is preferably sized so that it extends over the entire upper surface of the table 402 so as to completely cover the patient 400. As such, the end 422 will extend at least to cover the patient's head, the foot end 424 will extend at least to cover the patient's feet, the lower sides 426a and 427a will extend at least to cover the patient's torso and legs, and the upper sides 426b and 427b will extend at least to cover the patient's extended arms. More preferably, the drape 421, at the foot end 424 and lower sides 426a and 427a, hangs well below the edge of the table 402.

In order to provide access to the patient 400 for performing surgery at a surgical site 462, the drape 421 is formed with a cutout or window 464. An attachment device 466, such as one or more adhesive strips, may be provided around the edge of the cutout 464 in order to secure the drape 421 to the patient, and provide a seal that isolates the surgical site and keeps the inflating medium away from it. Because the drape 421 is not inflatable, it may be pressed flush against the patient 400 around the periphery of the cutout 464, and optionally secured, so that unobstructed access to the patient is ensured.

The drape 421 is employed for the same purposes as surgical drapes that are known in the art. The drape 421 also helps retain the inflating medium proximate to the patient body. Air that is exhausted from the inflatable thermal blanket 420 flows beyond the edge thereof and beneath the drape 421, where it is maintained in proximity to the patient 400. At the head end 422, it is necessary to keep the drape 421 away from the patient's nose and mouth, so that respiration is not affected. For that purpose, a frame structure, which may be formed by a pair of vertical posts 468 mounted on the table 402, is provided. The head end 422 of the surgical barrier device 419 may be wrapped around the posts 468 and secured using tape 470 or any other appropriate fastening device, such as clips, etc.

As shown in FIG. 12, the inflatable thermal blanket 420 is inflated, during use, with the inflating medium. When inflated, the inflatable thermal blanket 420 is positioned over the patient's chest and upper extremities. The drape 421 advantageously covers the patient 400 and hangs downwardly along the sides and foot end of the table 402 to help retain the inflating medium on the patient.

The inflatable thermal blanket 420 and the drape 421 may be formed in any of the ways shown in FIGS. 18-23, and described above in connection with the drape 321 and the inflatable thermal blanket 320.

Figures 14, 15:
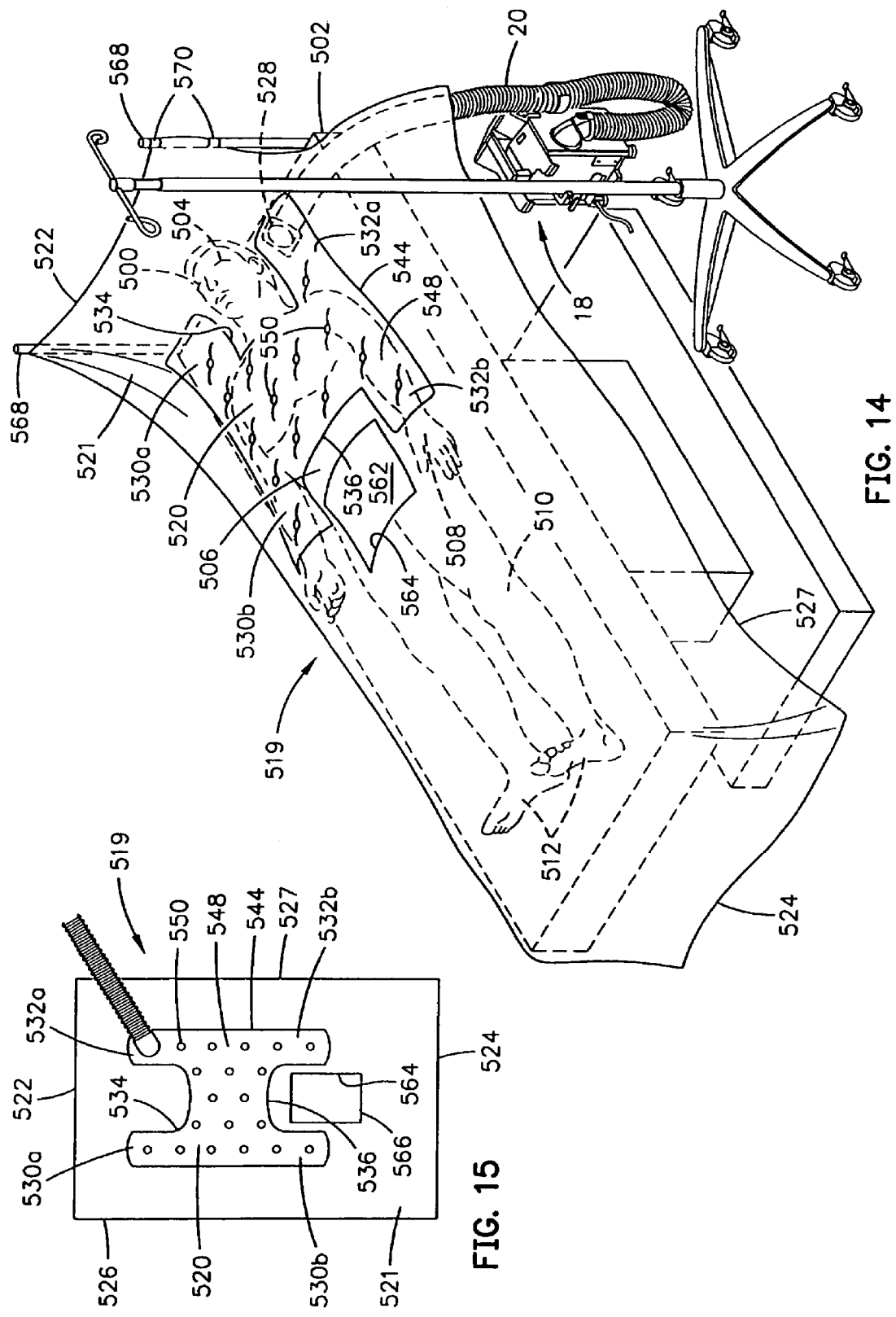
FIG. 14 is a perspective view of a third embodiment of a surgical barrier device constructed in accordance with the invention, for thermally bathing a patient using an inflatable cover for covering the torso and upper extremities of the patient, and a drape for covering additional portions of the patient's body, while providing medical access to the patient.
FIG. 15 is a diagrammatic plan view of the surgical barrier device of FIG. 14.

FIGS. 14 and 15 illustrate a third embodiment of the surgical barrier device 519 for use in pelvic and groin surgery, in which an inflatable thermal blanket 520 is deployed for thermally bathing the torso and upper extremities of a patient, and a drape 521 is deployed for covering additional portions of the patient's body, while performing barrier functions and providing access to a surgical site in the patient's pelvis and groin.

In FIG. 14, a patient 500 is reclined on an examination table 502. The patient's head 504 lies prone on the table 502, as do the patient's torso 506, arms 508, legs 510 and feet 512. The patient's arms 508 lie at the patient's side and the patient's feet 512 are slightly apart. The surgical barrier device 519 that includes the inflatable thermal blanket 520, and the surgical drape 521, is deployed over the patient 500. The thermal blanket is constructed to warm convectively by exhausting warm air onto the patient 500. The inflatable thermal blanket 520 is similar in most respects to the inflatable thermal blankets shown in the preceding embodiments except that it is configured to have an inflatable portion for covering the patient's torso and upper extremities, while the drape 521 covers additional portions of the patient. As in the case of the embodiments disclosed above, the surgical barrier device 519 includes ends 522 and 524, a pair of outer lateral edges or sides 526 and 527, and an inflation inlet cuff 528 that opens into the inflatable thermal blanket 520. The inflation cuff 528 may be connected through a flexible heater hose, such as the heater tube 20 to the heater/blower assembly 18, the construction of which is described above in connection with FIG. 1. In FIG. 14, the inlet cuff 528 is shown mounted on the underside of the blanket 520, but it could also be mounted on the upperside of the blanket.

The inflatable thermal blanket 520 includes upper elongated portions 530a and 532a and lower elongated portions 530b and 532b. An upper central recess 534 is disposed between the upper elongated portions 530a and 532a. A lower central recess 536 is disposed between the lower elongated portions 530b and 532b. The upper recess 534 provides an area for viewing the patient's head 504. The lower recess 536 provides an area for viewing or accessing a care site.

The inflatable thermal blanket 520 is formed as an inflatable covering that includes a flexible upper sheet and a flexible base sheet that are identical to the upper and base sheets 340 and 342 shown in FIGS. 18 and 19. These sheets are secured to each other along a peripheral seam 544 that extends around the periphery of the inflatable portion. The peripheral seam 544 can be formed by a heat sealing process as described above. It is preferably continuous, but may also be formed with interruptions at selected locations thereof to facilitate egress of the inflating medium, e.g., heated air, as described above. The upper and base sheets of the inflatable thermal blanket 520 are constructed using the materials and techniques described above in connection with FIGS. 2-4, forming a parallel array of elongated tubes using seams formed by elongated heat seals as shown in FIGS. 1-4, or an array of quasi-discrete inflatable chambers 548 formed using point seals 550, as shown in FIGS. 14 and 15. A plurality of apertures identical to the apertures 352 shown in FIGS. 18 and 19 open through the base sheet into the inflatable thermal blanket 520. The apertures convectively deliver the inflating medium into the interior space surrounding the patient, which is enclosed by the surgical barrier device 519. The base sheet of the inflatable thermal blanket 520 is preferably constructed like the base sheet of FIG. 3, which comprises an underside layer 50 made from a flexible, fibrous material, and an upperside layer 52 made from a heat-sealable synthetic material. The apertures may be formed as holes extending through both of the layers 50 and 52 of this base sheet. Alternatively, the apertures may be formed as holes extending through the upper layer 52, and as spaces which naturally occur between the fibers of the fibrous material used to form the underside layer 50.

The surgical drape 521 is attached to, or formed integrally with, the inflatable thermal blanket 520. The drape 521 extends from the periphery of the inflatable thermal blanket, including the recesses 534 and 536, and extends outwardly to define the head end 522, the foot end 524, and the sides 526 and 527 of the surgical barrier device 519. As shown in FIG. 15, the drape 521 is rectangular in shape. It is preferably sized so that it extends over the entire upper surface of the table 502 so as to completely cover the patient 500. As such, the end 522 will extend at least to cover the patient's head, the end 524 will extend at least to cover the patient's feet, and the sides 526 and 527 of the blanket will extend at least to cover the patient's legs and arms. More preferably, the drape 521, at the foot end 524 and sides 526 and 527, hangs well below the edge of the table 502.

In order to provide access to the patient 500 for performing surgery at a surgical site 562, the drape 521 is formed with a cutout or window 564. An attachment device 566, such as one or more adhesive strips, may be provided around the edge of the cutout 564 in order to secure the drape 521 to the patient and provide a seal that isolates the surgical site, and keeps the inflating medium away from it. Because the drape 521 is not inflatable, it may be pressed flush against the patient 500 around the periphery of the cutout 564, and optionally secured, so that unobstructed access to the patient is ensured.

The drape 521 is employed for the same purposes as surgical drapes that are known in the art. The drape 521 also helps retain the inflating medium proximate to the patient body. Air that is exhausted from the inflatable thermal blanket 520 flows beyond the edge thereof and beneath the drape 521, where it is maintained in proximity to the patient 500. At the head end 522, it is necessary to keep the drape 521 away from the patient's nose and mouth so that respiration is not affected. For that purpose, a frame structure, which may be formed by a pair of vertical posts 568 mounted on the table 502, is provided. The head end 522 may be wrapped around the posts 568 and secured using tape 570 or any other appropriate fastening device, such as clips, etc.

As shown in FIG. 14, the inflatable thermal blanket 520 is inflated during use, with the inflating medium. When inflated, the inflatable thermal blanket 520 is positioned over the patient's torso and upper extremities. The drape 521 advantageously covers the patient 500 and hangs downwardly along the sides and foot end of the table 502 to help retain the inflating medium on the patient.

The inflatable thermal blanket 520 and the drape 521 can be formed in any of the ways shown in FIGS. 18-23, and described above in connection with the drape 321 and the inflatable thermal blanket 320.

Figure 16:
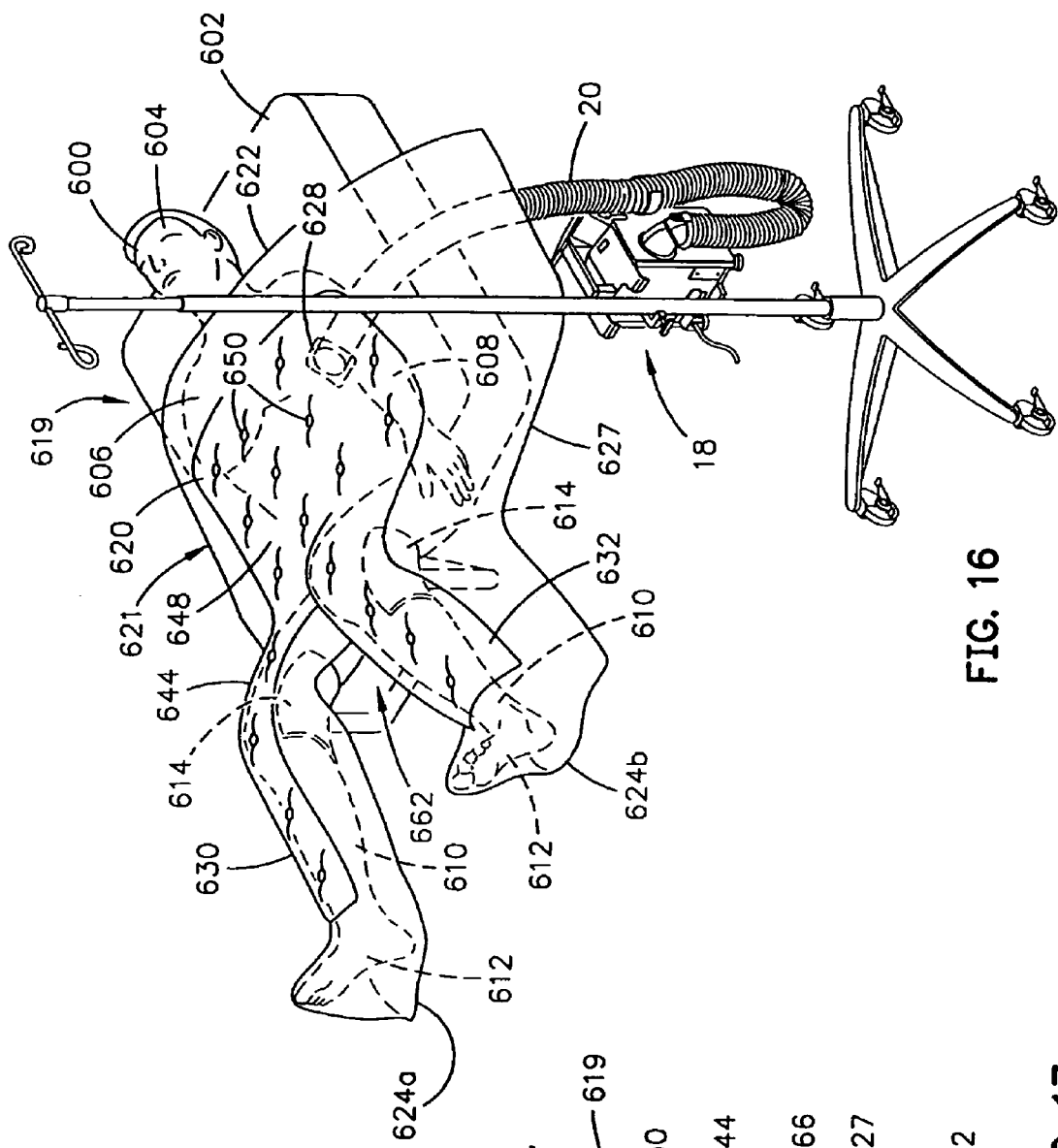
FIG. 16 is a perspective view of a fourth embodiment of a surgical barrier device constructed in accordance with the invention, for thermally bathing a patient using an inflatable cover for covering the torso, upper extremities and lower extremities of the patient, and a drape for covering additional portions of the patient's body while providing medical access to the patient.
Figure 17:
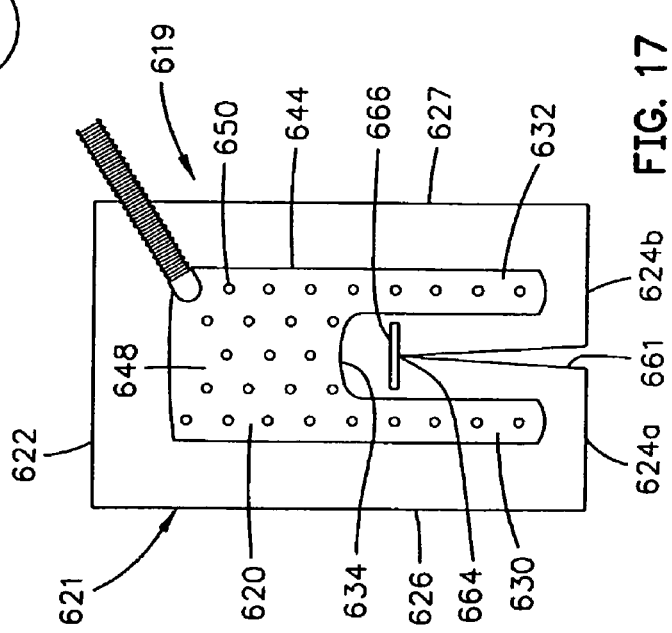
FIG. 17 is a diagrammatic plan view of the surgical barrier device of FIG. 16.

FIGS. 16 and 17 illustrate a fourth embodiment of the surgical barrier device 619 for use in lithotomy surgery, in which an inflatable thermal blanket 620 is deployed for thermally bathing the torso, upper extremities and lower extremities of a patient, and a surgical drape 621 is deployed for covering additional portions of the patient's body, while performing barrier functions and providing access to a surgical site in the patient's groin and genital area.

In FIG. 16, a patient 600 is reclined in the lithotomy position on an examination table 602. The patient's head 604 lies prone on the table 602, as do the patient's torso 606 and arms 608. The patient's legs 610 and feet 612 extend upwardly and apart and are supported by stirrups 614 that are mounted on the table 602. The patient's arms 608 lie at the patient's side and the patient's feet 612 are spread widely apart to facilitate access to the patient's perineal region, genitals and rectum. The surgical barrier device 619 that includes the inflatable thermal blanket 620, and the surgical drape 621, is deployed over the patient 600. The thermal blanket is constructed to warm convectively by exhausting warm air onto the patient 600. The inflatable thermal blanket 620 is similar in most respects to the inflatable thermal blankets shown in the preceding embodiments except that it is configured to have an inflatable portion for covering the patient's torso, upper extremities and lower extremities, while the drape 621 covers additional portions of the patient. As in the case of the embodiments disclosed above, the surgical barrier device 619 includes a first end 622, a bifurcated foot end formed by two adjacent foot end portions 624a and 624b, a pair of outer lateral edges or sides 626 and 627 and an inflation inlet cuff 628 that opens into the inflatable thermal blanket 620. The inflation cuff 628 may be connected through a flexible heater hose, such as the heater tube 20, to the heater/blower assembly 18, the construction of which is described above in connection with FIG. 1. In FIG. 16, the inlet cuff 628 is shown mounted to the underside of the blanket 620, but it could also be mounted to the upperside of the blanket.

The inflatable thermal blanket 620 includes elongated portions 630 and 632 separated by a central opening 634.

The inflatable thermal blanket 620 is formed as an inflatable covering that includes a flexible upper sheet and a flexible base sheet that are identical to the upper and base sheets 340 and 342 shown in FIGS. 18 and 19. These sheets are secured to each other along a peripheral seam 644 that extends around the periphery of the inflatable portion. The peripheral seam 644 can be formed by a heat sealing process as described above. It is preferably continuous, but may also be formed with interruptions at selected locations thereof to facilitate egress of the inflating medium, e.g., heated air, as described above. The upper and base sheets of the inflatable thermal blanket 620 are constructed using the materials and techniques described above in connection with FIGS. 2-4, forming a parallel array of elongated tubes using seams formed by elongated heat seals as shown in FIGS. 1-4, or an array of quasi-discrete inflatable chambers 648 formed using point seals 650, as shown in FIGS. 16 and 17. A plurality of apertures identical to the apertures 352 shown in FIGS. 18 and 19 open through the base sheet into the inflatable thermal blanket 620. The apertures convectively deliver the inflating medium into the interior space surrounding the patient, which is enclosed by the surgical barrier device 619. The base sheet of the inflatable thermal blanket 620 is preferably constructed like the base sheet of FIG. 3, which comprises an underside layer 50 made from a flexible, fibrous material, and an upperside layer 52 made from a heat-sealable synthetic material. The apertures may be formed as holes extending through both of the layers 50 and 52 of this base sheet. Alternatively, the apertures may be formed as holes extending through the upper layer 52, and as spaces which naturally occur between the fibers of the fibrous material used to form the underside layer 50.

The surgical drape 621 is attached to, or formed integrally with, the inflatable thermal blanket 620. The drape 621 extends from the periphery of the inflatable thermal blanket 620, including the recess 634, and extends outwardly to define the head end 622 and the sides 626 and 627 of the surgical barrier device 619. The foot end portions 624a and 624b are separated by a longitudinal V-shaped cutout 661 that extends from the ends of the foot end portion to a point adjacent the head end of the recess 634. As shown in FIG. 17, the drape 621 is rectangular at the head end 622 and has two elongated extensions at the foot end portions 624a and 624b. It is preferably sized so that it covers a majority of the upper surface of the table 602 so as to cover all of the patient 600 except for the patient's head 604. As such, the end 622 will extend at least to cover the patient's shoulders, the foot end portions 624a and 624b will extend at least to cover the patient's feet, and the sides 626 and 627 will extend to at least cover the patient's legs and arms. More preferably, the drape 621 at the foot end portions 624a and 624b, and the sides 626 and 627, hangs well below the edge of the table 602.

In order to provide access to the patient 600 for performing surgery at a surgical site 662, the drape 621 is formed with the V-shaped cutout 661, and an additional transverse slit 664 formed at the head end of the V-shaped cutout. An attachment device 666, such as one or more adhesive strips, may be provided along the head end of the slit 664 in order to secure the drape 621 to the patient and provide a seal that isolates the surgical site and keeps the inflating medium away from it. Because the drape 621 is not inflatable, it may be pressed flush against the patient 600 at locations above the slit 664, and optionally secured, so that unobstructed access to the patient is ensured.

The drape is employed for the same purposes as surgical drapes that are known in the art. The drape 621 also helps retain the inflating medium proximate to the patient body. Air that is exhausted from the inflatable thermal blanket 620 flows beyond the edge thereof and beneath the drape 621, where it is maintained in proximity to the patient 600.

As shown in FIG. 16, the inflatable thermal blanket 620 is inflated, during use, with the inflating medium. When inflated, the inflatable thermal blanket 620 is positioned over the patient's torso, upper extremities and lower extremities. The drape 621 advantageously covers the patient 600 and hangs downwardly along the sides and foot end of the table 602 to help retain the inflating medium on the patient.

The inflatable thermal blanket 620 and the drape 621 can be formed in any of the ways shown in FIGS. 18-23, and described above in connection with the drape 321 and the inflatable thermal blanket 320.

Many modifications and variations of our invention will be evident to those skilled in the art. It is understood that such variations may deviate from specific teachings of this description without departing from the essence of the invention, which is expressed in the following claims.

I claim:

1. A combination for use during surgery on a person, comprising:
   a flexible base sheet;
   a material sheet attached to a first surface of the base sheet by a plurality of seals to form an inflatable portion with a periphery;
   a plurality of apertures through the base sheet within the periphery; and
   a surgical drape including a drape sheet of flexible material attached to the base sheet.

2. A surgical barrier device, comprising;
   an inflatable device that includes:
   a base sheet with two ends, two edges, and an undersurface;
   the ends, and respective edges of the base sheet forming a periphery;
   the base sheet including a layer of fibrous material on which the undersurface is disposed;
   a material sheet attached to the base sheet by a seal near the periphery;
   an inflating inlet for admitting a thermally controlled inflating medium into the inflatable device; and the base sheet adapted for exhausting the thermally controlled inflating medium from the inflatable device through the undersurface;

the inflatable device being sized and configured to cover one or more partial portions of a body; and a surgical drape including a surgical drape sheet of material attached to the inflatable device and extending beyond the periphery, the surgical drape being sized and configured to cover additional portions of the body; and an opening in the surgical drape for accessing a surgical site on the body.

3. A surgical barrier device in accordance with claim 2, wherein the surgical drape sheet of material is attached to the base sheet.

4. A surgical barrier device in accordance with claim 3, wherein the surgical drape sheet of material is attached to the material sheet.

5. A surgical barrier device in accordance with claim 4, wherein the surgical drape sheet of material is attached at an edge portion thereof to the material sheet near the periphery.

6. A surgical barrier device in accordance with claim 4, wherein the surgical drape sheet of material covers the material sheet and is attached to the material sheet near the periphery.

7. A surgical barrier device in accordance with claim 2, further including a plurality of seals between the material sheet and the base sheet within the periphery.

8. A surgical barrier device in accordance with claim 2 wherein the inflatable device is configured to cover the pelvic region and lower extremities of the body, and the surgical drape is generally rectangular in shape.

9. A surgical barrier device in accordance with claim 8, wherein the inflatable device has a recess at an end thereof, and the opening is adjacent to the recess.

10. A surgical barrier device in accordance with claim 2, wherein the inflatable device is configured to cover the chest and upper extremities of the body, and the surgical drape is generally rectangular in shape.

11. A surgical barrier device in accordance with claim 2, wherein the inflatable device has a recess at a first end thereof and a recess at a second end thereof, and the opening is adjacent to the second end recess.

12. A surgical barrier device in accordance with claim 2, wherein the inflatable device is configured to cover the torso and upper extremities of the body, and the surgical drape is generally rectangular in shape.

13. A surgical barrier device in accordance with claim 12, wherein the inflatable device has a recess at a first end thereof and a recess at a second end thereof, and the opening is adjacent to the second end recess.

14. A surgical barrier device in accordance with claim 2, wherein the inflatable device is configured to cover the torso, the upper extremities and the lower extremities of the body, and the surgical drape has a generally rectangular head end portion and a pair of foot end portions separated by the opening.

15. A surgical barrier device in accordance with claim 14, wherein the inflatable device has a recess at an end thereof, and the opening is adjacent to the recess.

16. A surgical barrier device in accordance with claim 15, wherein the opening includes a longitudinal V-shaped notch and a transverse slit intersecting the head end of the notch.

17. A surgical barrier device in accordance with claim 2, further including a frame for supporting an end of the surgical drape.

* * * * *

UNITED STATES PATENT AND TRADEMARK OFFICE
CERTIFICATE OF CORRECTION

| | | |
|---|---|---|
| PATENT NO. | : 7,871,428 B2 | Page 1 of 1 |
| APPLICATION NO. | : 11/511918 | |
| DATED | : January 18, 2011 | |
| INVENTOR(S) | : Scott Douglas Augustine | |

It is certified that error appears in the above-identified patent and that said Letters Patent is hereby corrected as shown below:

Column 2
Line 24, delete "drape," and insert -- drape. --, therefor.

Column 3
Line 16, after "constructed" insert -- inflatable --.

Column 4
Line 19, after "Blankets" insert -- : --.

Column 10
Line 18, delete "364," and insert -- 364. --, therefor.

Signed and Sealed this
Fourth Day of September, 2012

David J. Kappos
*Director of the United States Patent and Trademark Office*